United States Patent
Johnson et al.

(10) Patent No.: US 7,288,698 B2
(45) Date of Patent: Oct. 30, 2007

(54) ALFALFA PLANTS HAVING IMPROVED STANDABILITY AND METHODS FOR PRODUCING SAME

(75) Inventors: David W. Johnson, West Salem, WI (US); Mark E. Darling, Woodland, CA (US); Douglas K. Miller, West Salem, WI (US); Jonathan M. Reich, Woodland, CA (US)

(73) Assignee: Cal/West Seeds, Woodland, CA (US)

( * ) Notice: Subject to any disclaimer, the term of this patent is extended or adjusted under 35 U.S.C. 154(b) by 0 days.

(21) Appl. No.: 11/367,405

(22) Filed: Mar. 6, 2006

(65) Prior Publication Data

US 2006/0206970 A1    Sep. 14, 2006

Related U.S. Application Data

(62) Division of application No. 10/698,424, filed on Nov. 3, 2003.

(60) Provisional application No. 60/422,857, filed on Nov. 1, 2002.

(51) Int. Cl.
*A01H 5/00* (2006.01)
*A01H 5/10* (2006.01)
*C12N 15/82* (2006.01)

(52) U.S. Cl. ..................... 800/298; 435/410

(58) Field of Classification Search ............... 800/260, 800/298; 435/410
See application file for complete search history.

(56) References Cited

U.S. PATENT DOCUMENTS

2004/0093648 A1   5/2004   Johnson et al.
2006/0206969 A1   9/2006   Johnson et al.

OTHER PUBLICATIONS

Poehlman, J.M. and D.A. Sleper. 1995. Breeding Field Crops. 4th ed. Iowa State University Press, Ames, Iowa, p. 473.*
Barnes et al. 1977. Alfalfa germplasm in the United States: Genetic vulnerability, use, improvement, and maintenance. USDA Tech. Bull. 1571, 21 pages.*
Julier et al. 2000. Crop Sci. 40: 365-369.*
Barnes et al., "Highlights in the USA and Canada," Ch. 1, pp. 1-24, in Alfalfa and Alfalfa Improvement, Hanson et al., (eds.), American Society of Agrnomy, Monograph No. 29, (1988).
Pioneer Hi-Bred International Alfalfa Variety '54V54' 1 page.
"WinterGold." Online. www.naaic.org., 1 page, Jun. 21, 2006.
"5312" Online. www.naaic.org., 1 page, Jun. 21, 2006.
Quiros et al., The Genus *Medicago* and the Origin of the *Medicago sativa* Complex, Ch. 3, p. 93, in Alfalfa and Alfalfa Improvement, Hanson et al., (eds.), American Society of Agrnomy, Monograph No. 29, (1988).
Barnes et al., "Alfalfa Germplasm in the United States: Genetic Vulnerability, Use, Improvement, and Maintenance," *USDA Tech. Bull.* 1571, 21 pages, (1977).
Julier et al., "Within- and Among-Cultivar Genetic Variation in Alfalfa: Forage Quality, Morphology, and Yield," *Crop Sci.* 40:365-369 (2000).
Moutray et al., "Registration of Crop Cultivars," *Crop Sci.* 23 : 178-179 (1983).
Kalu et al., "Morphological stage of development as a predictor of Alfalfa herbage quality," *Crop Sci.* 23:1167-1172 (1983).
Kalu et al., "Quantifying morphological development of Alfalfa for studies of herbage quality," *Crop Sci.* 21:267-271 (1981).

* cited by examiner

*Primary Examiner*—David H. Kruse
*Assistant Examiner*—Keith O. Robinson
(74) *Attorney, Agent, or Firm*—Cooley Godward Kronish LLP

(57) ABSTRACT

The invention provides alfalfa plants having improved standability and/or fast recovery after spring green-up or after harvest and methods for producing such plants. Such alfalfa plants provide increased annual yield of high quality forage.

4 Claims, 1 Drawing Sheet

Alfalfa Variety Development

ALFALFA PLANTS HAVING IMPROVED STANDABILITY AND METHODS FOR PRODUCING SAME

CROSS-REFERENCE TO RELATED APPLICATION

This application is a divisional of U.S. patent application Ser. No. 10/698,424, filed Nov. 3, 2003, which claims benefit of U.S. Provisional Application No. 60/422,857, filed Nov. 1, 2002, each of which are herein incorporated by reference in their entireties.

FIELD OF THE INVENTION

This invention relates to the field of alfalfa plants, and more specifically to alfalfa germplasm and alfalfa varieties having improved standability and/or fast recovery after spring green-up or fast recovery after harvest and methods for producing such improved germplasm and varieties.

BACKGROUND OF THE INVENTION

All publications and patent applications herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

Alfalfa (*Medicago sativa* L.) is an important forage species for hay and pasture which has been referred to as the "Queen of the Forages" because of its high yields and feeding value. Alfalfa is recognized as the most widely adapted agronomic crop, as an effective source of biological nitrogen ($N_2$) fixation, useful in the improvement of soil tilth, as an important source of protein yield/ha, and as an attractive source of nectar for honey bees. For a comprehensive review of the benefits of alfalfa as an agronomic crop, see Barnes et al., *Highlights in the USA and Canada* 1:2-24, In *Alfalfa and Alfalfa Improvement*, Hanson et al. (ed.), American Society of Agronomy, Monograph No. 29 (1988).

Although alfalfa originated in southwestern Asia, it is well adapted to a wide range of climates and soils in the United States. Alfalfa is classified into fall dormancy groups, numbered 1 to 10 that can be fitted into the plant hardiness zone map. Dormancy group 1 is very dormant and suited for cold climates (such varieties stop growing and go dormant over winter), and dormancy group 10 is very non-dormant and suited for very hot climates (such varieties have high growth rates over a very long growing season and would have relatively high winter activity). For a comprehensive review of geographic adaptation of alfalfa, see Melton et al., *Geographic Adaptation and Cultivar Selection* 20: 595-620, In *Alfalfa and Alfalfa Improvement*, supra. For a comprehensive review of the distribution, history and origin of alfalfa, see Michaud et al., *World Distribution and Historical Development* 2:25-91, In *Alfalfa and Alfalfa Improvement*, supra; and, Quiros et al., *The Genus Medicago and the Origin of the Medicago sativa Complex* 3:93-124, In *Alfalfa and Alfalfa Improvement*, supra.

The genus *Medicago* is widely distributed and comprises an array of diverse species that are either annual or perennial. The most recent taxonomic studies of the perennial species concluded that *M. sativa* is polymorphic. Lesins and Gillies (Taxonomy and cytogenetics of *Medicago* 353-386, In *Alfalfa science and technology*, C. H. Hanson (ed.), American Society of Agronomy, (1972)) defined the complex as *M. sativa-falcata-glutinosa*, and Gunn et al. (*USDA Tech. Bull. No.* 1574 (1978)) designated it as the *M. sativa sensu lato* complex.

*M. sativa* plants are autopolyploid organisms, or more specifically, autotetraploids. More specifically, *M. sativa* plants are polysomic polyploid organisms that display tetrasomic inheritance patterns.

Essentially all annual species are cleistogamous and are exclusively self-pollinated.

Generally, the perennial species require tripping, as by insect visits to the floral structures, and will set seed from either self or cross-pollination. Crosses can be made among subspecies in the *M. sativa* complexes and between the cultivated tetraploids and wild diploids without special preparation of the parents. For a comprehensive review of the floral characteristics, plant culture, and methods of self-pollinating or hybridizing alfalfa, see D. K. Barnes, *Alfalfa* 9:177-187, In *Hybridization of Crop Plants*, Fehr et al. (ed.), American Society of Agronomy Inc. (1980).

Commercial alfalfa seed may be provided either in a synthetic variety or a hybrid variety. Commercial production of synthetic varieties may include a breeder seed production stage, a foundation seed production stage, a registered seed production stage and a certified seed production stage. Hybrid variety seed production may involve up to three stages including a breeder seed production stage, a foundation seed production stage and a certified seed production stage.

Efforts in developing healthy and productive alfalfa varieties often focus on breeding for disease and stress-resistant cultivars, for example, breeding for persistence, breeding for adaptation to specific environments, breeding for yield per se, and breeding for quality. Between 1900 and 1975 more than 160 cultivars were developed for production in North America. Most of the newer cultivars were selected for improved adaptation and multiple pest resistance. Success has been attained in breeding for resistance to fungal, bacterial, insect, and nematode pests, including, but not limited to the development of varieties tolerant/resistant to bacterial wilt and common leaf spot (see, e.g., Elgin, Jr., et al., *Breeding for Disease and Nematode Resistance* 827-858, In *Alfalfa and Alfalfa Improvement*, supra) and to the spotted alfalfa aphid and alfalfa weevil (see, e.g., Sorensen et al., *Breeding for Insect Resistance* 859-902, In *Alfalfa and Alfalfa Improvement*, supra). Breeders have had less success in breeding for yield and quality per se (see, e.g., Hill et al., *Breeding for Yield and Quality* 26:809-825, In *Alfalfa and Alfalfa Improvement*, supra), although methods have been developed that help increase productivity and yield (U.S. Pat. No. 4,045,912). Historically, yield and productivity, quality and persistence are objectives of high concern to farmers.

Many factors affect the yield, productivity and quality of alfalfa harvests. One of the many factors affecting the quality of an alfalfa harvest is the stage of development or physiological maturity of the plant at harvest time (Kalu et al., Crop Science, Vol. 23, 1167-1172, December 1983). This dependency on stage of development suggests that herbage quality can be predicted by the maturity stage of the alfalfa. And in fact, methods of classifying the morphological stage of alfalfa have been developed to assist in the prediction of herbage quality (Kalu et al., Crop Science, Vol. 21, 267-271 (March-April 1981)).

Another factor that affects yield and quality is plant lodging that can result in plant stubble being left in the field at harvest time. Lodged or downed alfalfa causes great losses to farmers because it increases mowing time and results in reductions of both the yield and the quality of the harvested crop. University research has shown that an unharvested 7-inch stubble versus a clean cut 2-inch stubble can reduce forage yield by up to one third. Thus, alfalfa plants with improved standability are desirable because they require less mowing time and have a higher forage yield with improved forage quality.

Recovery time between harvests also limits overall alfalfa yields. A faster recovery between harvest shortens the number of days between harvests, which therefore maximizes the number of harvests and net yield for each season. Growers recognize and value the importance of this characteristic for its contribution to the season's net yield per acre. Additionally, fast recovery also contributes to moisture conservation, weed control and forage quality.

The "French" types of alfalfa include Flemish (or Flamande), Poitou, and Provence. North American alfalfa breeders have generally grouped the French alfalfa lines, including the French varieties 'Europe' (or 'Europa') and 'Mercedes', into the Flemish type. Flemish-type alfalfa varieties are characterized as being fast to recover after cutting, early to mature, vigorous, generally resistant to foliar diseases, susceptible to root and crown diseases, and moderately winter hardy. However, the Flemish-type alfalfa varieties are not considered to be adapted to North American growing conditions (see, e.g., Barnes et al., Alfalfa germplasm in the United States: Genetic vulnerability, use, improvement, and maintenance. USDA Tech. Bull. 1571, 21 pages (1977); Miller, D. and B. Melton, Description of Alfalfa Germplasm Culitvars and Germplasm Sources. New Mexico Agric. Exp. Stn. Special Report 53, 497 pages (1983)). Thus, while the French alfalfa varieties have some characteristics that would be beneficial for alfalfa production in the United States and Canada, they are not directly useful as North American alfalfa varieties due to their non-adaptability to its production and growing conditions.

As demonstrated by this review, there is a real need for alfalfa varieties with improved standability and/or faster recovery after spring green-up or faster recovery after harvest. The present invention provides alfalfa plants with improved standability and faster recovery after spring green-up or after harvest and methods of selection, breeding and production that use such plants. The alfalfa plants provided by this invention will reduce field losses from downed alfalfa, and provide for a better season long-distribution of yield, faster ground cover after spring green-up or after harvest, flexible harvest window, more net yield each season, equipment and labor efficiencies and management flexibility.

SUMMARY OF THE INVENTION

This invention provides alfalfa plants and alfalfa varieties having improved recovery after spring green-up or after harvest when compared to adapted commercial alfalfa plants and alfalfa varieties grown under the same field growing conditions in North America.

This invention provides alfalfa varieties that have on average about 8% or greater faster recovery after spring green-up or after harvest compared to an adapted commercial alfalfa variety grown under the same field growing conditions in North America. This invention further provides such alfalfa varieties that have on average about 9%, 10%, 15%, 20%, 25%, or 30% or greater faster recovery after spring green-up or after harvest.

This invention provides alfalfa varieties that have on average about 8% or greater faster recovery after spring green-up or after harvest compared to an adapted commercial alfalfa variety grown under the same field growing conditions in North America, wherein the adapted commercial variety is 'WinterGold', 'WL325HQ', 'WL319HQ' and/or 'Hybri-Force 400'. This invention further provides such alfalfa varieties that have on average about 9%, 10%, 15%, 20%, 25%, or 30% or greater faster recovery after spring green-up or after harvest.

This invention provides alfalfa varieties that have on average about 15% or greater more erect stems at late bloom compared to an adapted commercial alfalfa variety grown under the same field growing conditions in North America. This invention further provides such alfalfa varieties that have on average about 20%, 25%, 30%, 35%, 40%, 45%, 50%, 55%, 60% or greater more erect stems.

This invention provides alfalfa varieties that have on average about 15% or greater more erect stems at late bloom compared to an adapted commercial alfalfa variety grown under the same field growing conditions in North America, wherein the adapted commercial variety is 'WinterGold', 'WL325HQ', 'WL319HQ' and/or 'Hybri-Force 400'. This invention further provides such alfalfa varieties that have on average about 20%, 25%, 30%, 35%, 40%, 45%, 50%, 55%, 60% or greater more erect stems.

This invention provides alfalfa varieties with the following characteristics:
  a) on average about 8%, or 9%, or 10%, or 15%, or 20%, or 25%, or 30% or greater faster recovery after spring green-up or after harvest compared to an adapted commercial variety grown under the same field growing conditions in North America; and
  b) on average about 15%, or 20%, or 25%, 30%, 35%, 40%, 45%, 50%, 55%, 60% or greater more erect stems at late bloom compared to an adapted commercial variety grown under the same field growing conditions in North America.

This invention provides alfalfa varieties with the following characteristics:
  a) on average about 8%, or 9%, or 10%, or 15%, or 20%, or 25%, or 30% or greater faster recovery after spring green-up or after harvest compared to an adapted commercial variety grown under the same field growing conditions in North America, wherein the adapted commercial variety is 'WinterGold', 'WL325HQ', 'WL319HQ' and/or 'Hybri-Force 400'; and
  b) on average about 15%, or 20%, or 25%, 30%, 35%, 40%, 45%, 50%, 55%, 60% or greater more erect stems at late bloom compared to an adapted commercial variety grown under the same field growing conditions in North America, wherein the adapted commercial variety is 'WinterGold', 'WL325HQ', 'WL319HQ' and/or 'Hybri-Force 400'.

The invention also provides any of the reproductive and regenerative parts of any of the alfalfa varieties of the present invention, including but not limited to plant cells (in vivo and in vitro), cell cultures, plant parts, plant tissues and tissue cultures. Examples of such plant cells, plant tissues or plant parts include but are not limited to pollen, ovary, ovules, cotyledons, seeds, seedlings, leaflets, leaves, petioles, stems, branches, stipules, and the like.

In yet another embodiment, the present invention provides a tissue culture of regenerable cells of an alfalfa plant obtained from the alfalfa varieties of the present invention, wherein the tissue regenerates plants having all or substantially all of the morphological and physiological characteristics of the alfalfa plants provided by the present invention. In one such embodiment, the tissue culture is derived from a plant part selected from the group consisting of leaves, roots, root tips, root hairs, anthers, pistils, stamens, pollen, ovules, flowers, seeds, embryos, stems, buds, cotyledons, hypocotyls, cells and protoplasts. In another such embodiment, the present invention includes an alfalfa plant regenerated from the above described tissue culture.

This invention provides the cells, cell culture, tissues, tissue culture, seed, whole plant and plant parts of alfalfa germplasm designated 'CW 75046' and having ATCC Accession No. PTA-5346.

This invention provides the cells, cell culture, tissues, tissue culture, seed, whole plant and plant parts of alfalfa germplasm designated 'CW 83201' and having ATCC Accession No. PTA-5347.

This invention provides the cells, cell culture, tissues, tissue culture, seed, whole plant and plant parts of alfalfa germplasm designated 'CW 85029' and having ATCC Accession No. PTA-5348.

This invention provides the cells, cell culture, tissues, tissue culture, seed, whole plant and plant parts of alfalfa germplasm designated 'CW 95026' and having ATCC Accession No. PTA-5349.

This invention also provides methods for producing first-generation synthetic varieties of alfalfa seed wherein the method involves crossing a first parent alfalfa plant with a second parent alfalfa plant and harvesting resultant first-generation (F1) hybrid alfalfa seed, wherein said first or second parent alfalfa plant is selected from one of the alfalfa varieties provided by this invention.

This invention also provides a cell, cell culture, tissue and/or tissue culture of regenerable cells, the cells comprising genetic material from a synthetic variety alfalfa plant named 'CW 75046', wherein the cells regenerate plants having all or substantially all of the morphological and physiological characteristics of the synthetic alfalfa variety named 'CW 75046', the seed of which have been deposited and have ATCC Accession No. PTA-5346.

This invention also provides a cell, cell culture, tissue, and/or tissue culture of regenerable cells, the cells comprising genetic material from a synthetic variety alfalfa plant named 'CW 83201', wherein the cells regenerate plants having all or substantially all of the morphological and physiological characteristics of the synthetic alfalfa variety named CW 83021, the seed of which have been deposited and have ATCC Accession No. PTA-5347.

This invention also provides a cell, cell culture, tissue and/or tissue culture of regenerable cells, the cells comprising genetic material from a synthetic variety alfalfa plant named 'CW 85029', wherein the cells regenerate plants having all or substantially all of the morphological and physiological characteristics of the synthetic alfalfa variety named 'CW 85029', the seed of which have been deposited and have ATCC Accession No. PTA-5348.

This invention also provides a cell, cell culture, tissue and/or tissue culture of regenerable cells, the cells comprising genetic material from a synthetic variety alfalfa plant named 'CW 95026', wherein the cells regenerate plants having all or substantially all of the morphological and physiological characteristics of the synthetic alfalfa variety named 'CW 95026', the seed of which have been deposited and have ATCC Accession No. PTA-5349.

This invention provides alfalfa varieties having high yield, persistence, multiple pest resistance, fast recovery after winter, improved standability and fast recovery after spring green-up or after harvest when compared to an appropriate check variety grown under the same field growing conditions in North America.

In a further aspect, the invention provides alfalfa plants useful for isolating genes, wherein the expression of the genes results in the production of alfalfa varieties having improved standability and/or fast recovery after spring green-up or after harvest when compared to an appropriate check variety grown under the same field growing conditions in North America.

In yet a further aspect, the invention provides plants useful for isolating genes that can be used to produce transgenic plants containing such genes, wherein the expression of the genes results in the production of alfalfa varieties having improved standability and/or fast recovery after spring green-up or after harvest when compared to an appropriate check variety grown under the same field growing conditions in North America.

In a further aspect, the invention contemplates feed for ruminants comprising the alfalfa varieties provided by the present invention. Alfalfa is a basic forage for maximizing ruminant animal production and provides an important source of nutrients for ruminant livestock such as dairy and beef cattle. Feed which includes alfalfa varieties of the present invention can take many forms including but not limited to greenchop, silage, hay, haylage, and dehydrated alfalfa, also called dehy.

In another embodiment, the invention also includes using the alfalfa varieties of the present invention in methods of producing animal feeds and in methods of administering such feeds to animals.

Although the present invention is broadly as defined above, it will be appreciated by those persons skilled in the art that it is not limited thereto and that it further includes the embodiments that are described below.

The methods of the present invention can be used to produce alfalfa plants with faster recovery after spring green-up or after harvest when compared to appropriate alfalfa check varieties.

Further objects and advantages of the present invention will be clear from the description that follows.

DETAILED DESCRIPTION OF THE INVENTION

Figure 1:
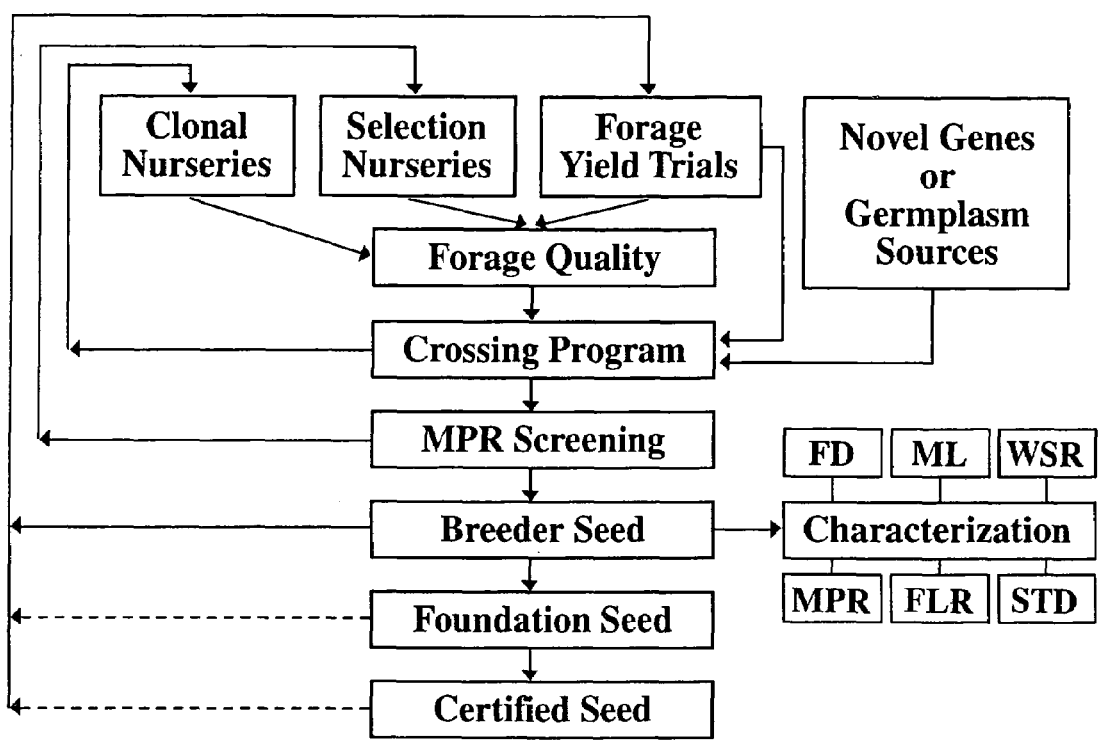
FIG. 1 is a schematic that details the major steps involved in the development of new alfalfa varieties. Key to "Characterization": FD=Fall Dormancy; ML=Multifoliolate Leaf Expression; WSR=Winter Survival Rating; MPR=Multiple Pest Resistance; FLR=Flowering or Maturity Stage; and STD=Standability Rating.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Overview of the Invention

Historically, improvements of yield, productivity and forage quality have been objectives of high concern to alfalfa breeders. The quest for improvements in these important traits has led to the alfalfa plants of the instant invention. The alfalfa plants of the instant invention are the first alfalfa varieties with adaptation to North America that combine improved standability with faster recovery after spring green-up or after harvest. These new alfalfa varieties offer high yield, persistence, a complete pest package, improved standability, and faster recovery after spring green-up or after harvest.

Prior to the instant invention, the standability differences between commercial alfalfa varieties has been so small that most alfalfa breeders do not even rate their varieties for this important trait. The improved standability of the alfalfa plants of the instant invention is even more useful when weather conditions are such that presently-available alfalfa varieties would typically lodge. The faster recovery after spring green-up or after harvest of the alfalfa varieties of the instant invention speed "green-up" by 3-5 days, which reduces the number of days to maturity and to the next cutting. This earlier maturity to harvest starts with the first crop and can give large acreage alfalfa growers or dairymen who use contract harvesters a head start each season. The days gained on each crop harvest helps maximize the number of cuts taken before the fall cut-off date for harvesting. Thus, the improved alfalfa plants of the present invention allow growers to capture more of the season's total yield on harvests subsequent to first cutting when the weather is usually more cooperative.

Agronomic benefits to growers of these alfalfa varieties include, but are not limited to, reduced field losses from downed alfalfa, a better season long distribution of yield, faster ground cover after spring green-up or after harvest, and a more flexible harvest window. Economic benefits include, but are not limited to, potential for more net yield each season, equipment and labor efficiencies, and management flexibility.

Definitions

As used herein, the term "alfalfa" means any *Medicago* species, including, but not limited to, *M. sativa*, *M. murex*, *M. falcata*, *M. prostrata* and *M. truncatula*. Thus, as used herein, the term "alfalfa" means any type of alfalfa including, but is not limited to, any alfalfa commonly referred to as cultivated alfalfa, diploid alfalfa, glanded alfalfa, purple-flowered alfalfa, sickle alfalfa, variegated alfalfa, wild alfalfa, or yellow-flowered alfalfa.

As used herein, the terms "lodging" or "lodged" mean the settling or collapse of a plant from an upright position. A plant is considered to be "lodged" to a given extent based on the proportion of it's stem(s) that have an angle with the ground of about 45° or less. Thus, according to this definition, a plant stem that has an angle with the ground of about 40° or less, or about 35° or less, or about 30° or less, or about 25° or less, or about 20° or less, or about 15° or less, or about 10° or less, or about 5° or less is considered to be lodged.

As used herein, the term "standability" means an alfalfa plant's resistance to lodging.

As used herein, the term "variety" means a subdivision of a species, consisting of a group of individuals within the species that is distinct in form or function from other similar arrays of individuals.

Seed Deposits

On Jul. 25, 2003, at least 2,500 seeds of each of four different alfalfa varieties were deposited under the conditions of the Budapest Treaty with the American Type Culture Collection (ATCC), 10801 University Blvd., Manassas, Va. 20110-2209. The following four seed deposits are exemplary of the instant invention:

Seed of alfalfa germplasm designated 'CW 75046' has been given ATCC No. PTA-5346.

Seed of alfalfa germplasm designated 'CW 83201' has been given ATCC No. PTA-5347.

Seed of alfalfa germplasm designated 'CW 85029' has been given ATCC No. PTA-5348.

Seed of alfalfa germplasm designated 'CW 95026' has been given ATCC No. PTA-5349.

Trait Determinations

The various plant ratings used herein are based on the North American Alfalfa Improvement Conference (NAAIC) Standard Tests To Characterize Alfalfa Cultivars (Third Edition, Amended 2002), except for the Recovery After Spring Green-up or After Harvest Rating and Standability Rating that are established by the methods disclosed herein.

Fall Dormancy (FD). The reaction of alfalfa varieties to decreasing daylength and temperatures in the fall versus check varieties. FD 1='Maverick'; FD 2='Vernal'; FD 3='5246'; FD 4='Legend'; FD 5='Archer'; FD 6='ABI 700'; FD 7='Dona Ana'; FD 8='Pierce'; FD 9='CUF10'; FD 10='UC-1887'; and FD 11='UC-1465'.

Winter Survival Rating (WSR). 1=most winter hardy and least winter injury and 6 least hardy and injury resulting in plant death. Ratings are in relationship to winter injury incurred by standard check varieties. WSR 1='Beaver' or 'Maverick' or 'ZG9830'; WSR 2='Vernal' or '526' or '5262'; WSR 3='Apica' or 'Ranger' or 'WL325HQ'; WSR 4='G-2852' or 'Fortress'; WSR 5='Archer' or 'Sutter'; and WSR 6='Cuf 101' or 'Moapa 69'.

Multifoliate Leaf Expression Rating (ML). Multifoliate refers to leaves with greater than 3 leaflets/leaf. The percentage of plants with at least one multifoliate leaflet per plant.

Multifoliate Index (MFI). The density of multileaflets per plant as compared to check varieties. Trifoliolate MFI 1.00='Vernal'; Low MFI 1.89='Legend'; Moderate MFI 2.55='MultiKing I'; and High MFI 3.34='Proof'.

Forage Quality was determined using Near Infrared Reflectance Spectroscopy or NIRS. NIRS was conducted according to Shenk, John S. and Mark O. Westerhaus, Forage Analysis by Near Infrared Spectroscopy, In Forages Vol. II 5th ed., Ed. Robert Barnes, Darrell A Miller, C Jerry Nelson published by Iowa State University Press, Ames Iowa (1995).

Milk per Ton=an excellent measure for ranking varieties for forage quality since fiber, not protein, is the first limiting factor in high performance rations. However, sacrificing yield to improve forage quality results in reduced profitability.

Milk per Acre=combines yield and quality into a single term. Milk per acre was calculated using forage quality weighted by yield of each cutting.

Pest Resistance Ratings—S=Susceptible with 0-5% resistant plants; LR=Low Resistance with 6-14% resistant plants; MR=Moderate Resistance with 15-30% resistant plants; R=Resistance with 31-50% resistant plants; and HR=High Resistance with greater than 50% resistant plants.

Yield=Forage Dry Matter tons/acre.

CP=Crude Protein.

ADF=Acid Detergent Fiber.

NDF=Neutral Detergent Fiber.

ADL=Acid Detergent Lignin.

NDFD=Neutral Detergent Fiber Digestibility.

RFQ=Relative Forage Quality.

Recovery After Spring Green-up or After Harvest (REC). Recovery after spring green-up or after harvest is the rate of re-growth after spring green-up or after harvest as determined by measuring plant height at varying intervals and then comparing growth with check varieties. Slow Recovery after spring green-up or after harvest='Vernal'; Moderate Recovery after spring green-up or after harvest='WinterGold' and 'Hybri-Force 400', Fast Recovery after spring green-up or after harvest='CW 75046' and 'CW 95026' and Very Fast Recovery after spring green-up or after harvest='CW 83201' and 'CW 85029'.

Standability Rating (STD). Standability of plants as determined by measuring the percent of stems standing >45° through late (i.e., 75%) bloom stage, wherein 9=high standability and 0=no standability. Rates are in relationship to standability of check varieties. No Standability 0='WL325HQ' and 'WL319HQ'; Low Standability 3='CW 83021' and 'CW 85029'; Moderate Standability 5='CW 75046' and 'CW 95026' (or 'Mercedes'); and High Standability (8)='CW 14032' and 'CW 15033' (or 'Europe').

As used herein, the "Standability Rating" of a plant is based on the average erectness of its stems through late (i.e., 75%) bloom. The actual Standability Rating of a particular plant is determined according to the following scale:

0=0 to 10% of stems are erect, 90 to 100% of stems are lodged.

1=11 to 20% of stems are erect, 80 to 89% of stems are lodged.

2=21 to 30% of stems are erect, 70 to 79% of stems are lodged.

3=31 to 40% of stems are erect, 60 to 69% of stems are lodged.

4=41 to 50% of stems are erect, 50 to 59% of stems are lodged.

5=51 to 60% of stems are erect, 40 to 49% of stems are lodged.

6=61 to 70% of stems are erect, 30 to 39% of stems are lodged.

7=71 to 80% of stems are erect, 20 to 29% of stems are lodged.

8=81 to 90% of stems are erect, 10 to 19% of stems are lodged.

9=91 to 100% of stems are erect, 0 to 9% of stems are lodged.

The following commercial alfalfa varieties are adapted for alfalfa production in North America and are appropriate as commercial checks for evaluating the standability and fast recovery of newly developed alfalfa varieties: 'WinterGold', 'WL325HQ', 'WL319HQ' and/or 'HybriForce 400' (sometimes designated as 'Hybri-Force 400').

EXAMPLES

Example 1

Alfalfa Varieties with Fast Recovery After Spring Green-up or After Harvest

Recovery after spring green-up or after harvest refers to the rate of regrowth after spring green-up or after harvest. This is determined by measuring plant height at varying intervals and then comparing growth with check varieties. In particular, after approximately 3-7 days the average height, to the nearest centimeter, of the plant canopy was measured. The measurement was repeated every few days through 21 days after the last cutting date.

The average height measurement was then converted to growth rate (cm/day) by dividing plant canopy height (cm) by the number of days since the last cutting. The average growth rate (cm/day) was then converted to a % of a comparison variety by dividing test variety growth rate by the comparison variety growth rate (cm/day) and then multiplying by 100.

TABLE 1

The recovery of alfalfa varieties 'CW 75046', 'CW 83201', and 'CW 85029' as compared to check variety 'WinterGold' when grown at the same time in the same location. E99WIWS - Spring Forage Yield Trial at West Salem, WI.

| Variety | Crops 2, 3, 4, average cm/day up to 21 days post harvest. | % of check WinterGold |
|---|---|---|
| CW 75046 | 2.37 | 108 |
| CW 83021 | 2.76 | 126 |
| CW 85029 | 2.80 | 127 |
| WinterGold | 2.19 | 100 |

TABLE 2

The recovery of alfalfa variety 'CW 95026' as compared to check variety 'WL325HQ' when grown at the same time in the same location. A00WIWS - Spring Forage Yield Trial at West Salem, WI.

| Variety | Crops 2, 3, 4, average cm/day up to 21 days post harvest. | % of check WL325HQ |
|---|---|---|
| CW 95026 | 2.56 | 131 |
| WL325HQ | 2.01 | 100 |

TABLE 3

The recovery of alfalfa varieties 'CW 75046', 'CW 83201', 'CW 85029', and 'CW 95026' compared to check varieties 'Vernal', 'WinterGold' and 'WL 325HQ' when grown at the same time in the same location. A01WIWS - Spring Forage Yield Trial at West Salem, WI.

| Variety | Crops 2, 3, 4, average cm/day up to 21 days post harvest. | % of check WinterGold |
|---|---|---|
| CW 75046 | 2.29 | 108 |
| CW 83021 | 2.69 | 127 |
| CW 85029 | 2.76 | 130 |
| CW 95026 | 2.56 | 120 |
| Vernal | 1.55 | 73 |
| WinterGold | 2.12 | 100 |
| WL 325HQ | 2.08 | 98 |

TABLE 4

The recovery of alfalfa varieties 'CW 75046', 'CW 83201', 'CW 85029', and 'CW 95026' compared to check varieties 'Daisy', 'Diane', 'Europe', 'Marshall', 'Mercedes', 'Vernal', 'WinterGold', and 'WL 325HQ' when grown at the same time in the same location. E01WIWS - Spring Forage Yield Trial at West Salem, WI.

| Variety | Crops 2, 3, average cm/day up to 21 days post harvest. | % of check WinterGold |
|---|---|---|
| CW 75046 | 1.94 | 112 |
| CW 83021 | 2.23 | 129 |
| CW 85029 | 2.31 | 134 |
| CW 95026 | 1.92 | 111 |
| Daisy | 1.44 | 083 |
| Diane | 1.57 | 091 |

TABLE 4-continued

The recovery of alfalfa varieties 'CW 75046', 'CW 83201', 'CW 85029', and 'CW 95026' compared to check varieties 'Daisy', 'Diane', 'Europe', 'Marshall', 'Mercedes', 'Vernal', 'WinterGold', and 'WL 325HQ' when grown at the same time in the same location. E01WIWS - Spring Forage Yield Trial at West Salem, WI.

| Variety | Crops 2, 3, average cm/day up to 21 days post harvest. | % of check WinterGold |
|---|---|---|
| Europe | 1.52 | 088 |
| Marshall | 1.48 | 085 |
| Mercedes | 1.52 | 088 |
| Vernal | 1.32 | 076 |
| WinterGold | 1.73 | 100 |
| WL 325HQ | 1.72 | 100 |

TABLE 5

The recovery of alfalfa varieties 'CW 83201' and 'CW 95026' compared to check varieties 'Evergreen', 'HybriForce 400', 'Vernal', 'WinterGold', and 'WL 325HQ' when grown at the same time in the same location. T01WIWS - Spring Forage Yield Trial at West Salem, WI.

| Variety | Crops 2, 3, average cm/day up to 21 days post harvest. | % of check WinterGold |
|---|---|---|
| CW 83021 | 2.61 | 137 |
| CW 95026 | 2.35 | 123 |
| Evergreen | 1.92 | 100 |
| HybriForce 400 | 1.87 | 098 |
| Vernal | 1.49 | 078 |
| WinterGold | 1.91 | 100 |
| WL 325HQ | 1.88 | 099 |

TABLE 6a

Spring Forage Yield Trial at West Salem. WI A01WIWS.

| Cut Date: | April 10 | | | May 27 | | | | June 30 | | |
|---|---|---|---|---|---|---|---|---|---|---|
| Measured Date: | April 29 | May 7 | May 12 | June 4 | June 9 | June 16 | June 20 | July 15 | | |
| # days | 19 | 27 | 32 | 8 | 13 | 20 | 24 | 15 | | |
| Entry | cm/day | cm/day | cm/day | cm/day | cm/day | cm/day | cm/day | cm/day | Ave. cm/day | CW 85029 % Faster |
| CW 85029 | 0.96 | 1.38 | 1.45 | 1.72 | 1.90 | 2.59 | 2.66 | 2.98 | 1.95 | 0.00 |
| CW 83021 | 0.95 | 1.38 | 1.41 | 1.72 | 1.83 | 2.58 | 2.71 | 2.98 | 1.94 | 0.58 |
| 5 Star | 0.91 | 1.27 | 1.33 | 1.41 | 1.79 | 2.36 | 2.49 | 2.73 | 1.79 | 9.45 |
| WL 342 | 0.87 | 1.17 | 1.23 | 1.25 | 1.44 | 2.06 | 2.36 | 2.53 | 1.62 | 20.99 |
| CW 95026 | 0.83 | 1.19 | 1.33 | 0.94 | 1.63 | 2.15 | 2.30 | 2.40 | 1.60 | 22.38 |
| CW 75046 | 0.86 | 1.24 | 1.33 | 1.09 | 1.46 | 2.21 | 2.30 | 2.18 | 1.58 | 23.33 |
| Geneva | 0.83 | 1.15 | 1.24 | 1.09 | 1.38 | 2.03 | 2.34 | 2.50 | 1.57 | 24.42 |
| Mountaineer | 0.83 | 1.10 | 1.20 | 1.09 | 1.31 | 1.98 | 2.25 | 2.43 | 1.52 | 28.22 |
| GH700 | 0.82 | 1.15 | 1.24 | 0.78 | 1.29 | 2.14 | 2.28 | 2.38 | 1.51 | 29.45 |
| Ascend | 0.78 | 1.16 | 1.24 | 0.63 | 1.31 | 2.04 | 2.25 | 2.48 | 1.48 | 31.62 |
| CW 05008 | 0.92 | 1.24 | 1.38 | 0.63 | 1.25 | 2.05 | 2.16 | 2.02 | 1.45 | 34.38 |
| Multiplier 3 | 0.71 | 1.06 | 1.12 | 0.78 | 1.21 | 2.08 | 2.17 | 2.42 | 1.44 | 35.55 |
| Magnum V | 0.83 | 1.15 | 1.27 | 0.47 | 1.21 | 1.99 | 2.32 | 2.15 | 1.42 | 37.26 |
| WL 325HQ | 0.79 | 1.06 | 1.16 | 0.63 | 1.19 | 1.96 | 2.21 | 2.20 | 1.40 | 39.62 |
| 512 | 0.78 | 1.06 | 1.18 | 0.31 | 1.23 | 2.03 | 2.31 | 2.20 | 1.39 | 40.84 |
| WinterGold | 0.71 | 1.06 | 1.10 | 0.63 | 1.21 | 1.93 | 2.08 | 2.23 | 1.37 | 42.72 |
| 54V54 | 0.78 | 1.06 | 1.21 | 0.31 | 1.15 | 1.84 | 2.13 | 2.23 | 1.34 | 46.05 |
| Radiant | 0.68 | 1.03 | 1.09 | 0.63 | 1.10 | 1.96 | 2.14 | 2.00 | 1.33 | 47.27 |
| A4230 | 0.64 | 0.98 | 1.07 | 0.63 | 1.08 | 1.83 | 2.13 | 2.10 | 1.31 | 49.64 |
| FQ 315 | 0.70 | 0.99 | 1.14 | 0.47 | 1.02 | 1.95 | 2.14 | 2.00 | 1.30 | 50.31 |
| CW 04007 | 0.76 | 1.05 | 1.24 | 0.31 | 1.12 | 1.84 | 2.07 | 2.00 | 1.30 | 50.48 |
| Magnum IV | 0.74 | 1.03 | 1.15 | 0.31 | 1.13 | 1.84 | 2.10 | 2.05 | 1.29 | 51.04 |
| Perfect | 0.67 | 1.06 | 1.15 | 0.47 | 1.15 | 1.76 | 1.95 | 2.00 | 1.28 | 53.03 |
| 5312 | 0.72 | 1.09 | 1.15 | 0.16 | 0.98 | 1.81 | 2.06 | 2.13 | 1.26 | 54.65 |
| 9429 | 0.66 | 1.03 | 1.10 | 0.31 | 0.96 | 1.71 | 2.11 | 2.02 | 1.24 | 57.85 |
| DK 142 | 0.68 | 0.95 | 1.09 | 0.47 | 0.85 | 1.91 | 2.04 | 1.85 | 1.23 | 58.72 |
| 54H69 (C) | 0.64 | 0.99 | 1.15 | 0.16 | 0.98 | 1.88 | 1.98 | 1.98 | 1.22 | 60.22 |
| BigHorn | 0.63 | 0.97 | 1.04 | 0.47 | 0.98 | 1.58 | 1.95 | 1.93 | 1.19 | 63.74 |
| FQ 314 | 0.68 | 0.94 | 1.06 | 0.16 | 0.94 | 1.73 | 2.08 | 1.85 | 1.18 | 65.49 |
| Ameristand 403T | 0.61 | 0.94 | 1.09 | 0.16 | 0.98 | 1.76 | 2.04 | 1.87 | 1.18 | 65.57 |
| EverGreen (C) | 0.62 | 0.99 | 1.03 | 0.31 | 0.87 | 1.68 | 2.02 | 1.82 | 1.17 | 67.56% |
| TMF 421 | 0.58 | 0.84 | 0.95 | 0.47 | 0.81 | 1.54 | 1.96 | 1.90 | 1.13 | 72.97 |
| Vernal | 0.55 | 0.80 | 0.93 | 0.00 | 0.87 | 1.49 | 1.96 | 1.50 | 1.01 | 93.27 |
| Mean | 0.76 | 1.09 | 1.19 | 0.74 | 1.23 | 1.97 | 2.20 | 2.23 | 1.43 | 40.44 |
| LSD (0.05) | 0.10 | 0.10 | 0.10 | 0.39 | 0.20 | 0.21 | 0.28 | 0.25 | 0.12 | |
| C.V. (%) | 9.22 | 6.52 | 5.71 | 37.01 | 11.68 | 7.67 | 9.04 | 8.01 | 6.18 | |
| R2 | 0.79 | 0.84 | 0.83 | 0.80 | 0.82 | 0.79 | 0.53 | 0.83 | 0.90 | |

TABLE 6b

Spring Forage Yield Trial at West Salem, WI. A02WIWS.

| Cut Date: | April 10: Greenup | | | May 27 Cut 1 | | | | June 30 Cut 2 | | |
|---|---|---|---|---|---|---|---|---|---|---|
| Measured Date: | April 29 | May 7 | May 12 | June 4 | June 9 | June 16 | June 20 | July 14 | | |
| # Days | 15 | 23 | 28 | 8 | 13 | 20 | 24 | 14 | | |
| Entry | cm/day | cm/day | cm/day | cm/day | cm/day | cm/day | cm/day | cm/day | Ave. cm/day | CW 85029 % Faster |
| CW 85029 | 1.33 | 1.62 | 1.61 | 1.72 | 1.77 | 2.51 | 2.65 | 2.59 | 1.97 | 0.00 |
| CW 15030 | 1.42 | 1.62 | 1.63 | 1.72 | 1.65 | 2.34 | 2.43 | 2.50 | 1.91 | 3.19 |
| CW 83021 | 1.35 | 1.59 | 1.60 | 1.56 | 1.62 | 2.40 | 2.51 | 2.18 | 1.85 | 6.71 |
| CW 15041 | 1.30 | 1.61 | 1.58 | 1.25 | 1.48 | 2.26 | 2.35 | 2.23 | 1.76 | 12.28 |
| CW 15031 | 1.32 | 1.53 | 1.53 | 1.09 | 1.56 | 2.08 | 2.29 | 2.38 | 1.72 | 14.72 |
| CW 15008 | 1.37 | 1.63 | 1.63 | 1.25 | 1.52 | 2.05 | 2.13 | 2.11 | 1.71 | 15.52 |
| CW 15040 | 1.33 | 1.59 | 1.58 | 0.78 | 1.52 | 2.15 | 2.33 | 2.38 | 1.71 | 15.64 |
| CW 15033 | 1.32 | 1.51 | 1.52 | 0.78 | 1.46 | 2.10 | 2.26 | 2.07 | 1.63 | 21.32 |
| CW 95026 | 1.23 | 1.46 | 1.45 | 0.94 | 1.25 | 2.05 | 2.31 | 2.32 | 1.63 | 21.43 |
| DK A42-15 | 1.18 | 1.43 | 1.46 | 1.09 | 1.40 | 1.99 | 2.15 | 2.20 | 1.61 | 22.44 |
| Ascend | 1.18 | 1.45 | 1.51 | 0.94 | 1.35 | 1.98 | 2.14 | 2.13 | 1.58 | 24.80 |
| Geneva | 1.22 | 1.40 | 1.35 | 0.94 | 1.19 | 2.05 | 2.21 | 1.93 | 1.54 | 28.59 |
| CW 75046 | 1.23 | 1.53 | 1.48 | 0.63 | 1.29 | 1.98 | 2.19 | 1.75 | 1.51 | 30.82 |
| CW 14032 | 1.17 | 1.45 | 1.46 | 0.63 | 1.21 | 2.01 | 2.14 | 2.02 | 1.51 | 30.87 |
| Setter | 1.05 | 1.36 | 1.41 | 0.63 | 1.21 | 1.88 | 2.20 | 2.25 | 1.50 | 31.86 |
| CW 15009 | 1.20 | 1.50 | 1.48 | 0.63 | 1.29 | 1.86 | 2.14 | 1.79 | 1.48 | 32.97 |
| CW 10090 | 1.13 | 1.42 | 1.40 | 0.63 | 1.19 | 1.93 | 2.15 | 1.84 | 1.46 | 35.16 |
| Prairie Max | 1.13 | 1.39 | 1.38 | 0.63 | 1.23 | 1.88 | 2.04 | 1.95 | 1.45 | 35.95 |
| Sommerset | 1.15 | 1.36 | 1.39 | 0.63 | 1.19 | 1.85 | 2.08 | 1.88 | 1.44 | 37.03 |
| CW 64010 | 1.05 | 1.34 | 1.35 | 0.63 | 1.21 | 1.80 | 2.08 | 2.04 | 1.44 | 37.46 |
| 54V54 | 1.10 | 1.33 | 1.36 | 0.47 | 1.15 | 1.90 | 2.01 | 2.07 | 1.42 | 38.71 |
| CW 10089 | 1.07 | 1.37 | 1.39 | 0.63 | 1.19 | 1.94 | 2.05 | 1.70 | 1.42 | 39.38 |
| Europe | 1.07 | 1.38 | 1.43 | 0.63 | 1.17 | 1.85 | 2.10 | 1.64 | 1.41 | 40.15 |
| WL 319HQ | 1.02 | 1.34 | 1.38 | 0.78 | 1.08 | 1.75 | 1.96 | 1.95 | 1.41 | 40.40 |
| Magnum IV | 1.22 | 1.39 | 1.43 | 0.31 | 1.23 | 1.78 | 1.93 | 1.96 | 1.41 | 40.45 |
| Supreme | 1.02 | 1.36 | 1.33 | 0.63 | 1.10 | 1.73 | 1.95 | 1.77 | 1.36 | 45.35 |
| CW 72009 | 1.02 | 1.27 | 1.26 | 0.63 | 1.13 | 1.84 | 1.93 | 1.79 | 1.36 | 45.48 |
| HybriForce-400 | 1.18 | 1.37 | 1.39 | 0.31 | 1.12 | 1.81 | 1.92 | 1.70 | 1.35 | 46.27 |
| Ameristand 403T | 0.90 | 1.14 | 1.16 | 0.00 | 0.94 | 1.53 | 1.72 | 1.64 | 1.13 | 74.91 |
| Vernal | 0.92 | 1.13 | 1.26 | 0.00 | 0.81 | 1.48 | 1.66 | 1.18 | 1.05 | 87.52 |
| | 1.11 | 1.39 | 1.40 | 0.79 | 1.26 | 1.90 | 2.08 | 1.97 | 1.49 | 36.18 |
| | 0.13 | 0.12 | 0.11 | 0.34 | 0.22 | 0.19 | 0.18 | 0.31 | 0.11 | |
| | 8.21 | 6.10 | 5.70 | 30.67 | 12.20 | 7.20 | 6.01 | 11.22 | 5.29 | |
| | 0.82 | 0.83 | 0.80 | 0.82 | 0.76 | 0.80 | 0.79 | 0.72 | 0.92 | |

Example 2

Alfalfa Varieties with Improved Standability

The following tables provide data demonstrating the improved standability of alfalfa varieties adapted to growing and production in North America. See the Definitions section, above, for the scale used in determining the Standability Ratings. Statistics (e.g., Grand Mean, LSD, C.V., R2) are based on the data collected for an entire trial.

TABLE 7a

The standability of alfalfa varieties 'CW 95026', 'CW 75046', 'CW 83201', and 'CW 85029' as compared to commercially available check varieties all grown at the same time in the same location. A01WIWS - Spring Forage Yield Trial at West Salem, WI.

| Date Last Cut/ Spring Greenup | May 21 | June 24 | August 28 | All Cuttings |
|---|---|---|---|---|
| # days growing | 34 | 30 | 47 | Ave. = 37 |
| Date Rated | June 24 | July 24 | October 14 | |

| Entry | Standability Ratings | | | |
|---|---|---|---|---|
| CW 05008 | 8.00 | 8.00 | 8.25 | 8.08 |
| CW 04007 | 7.50 | 7.50 | 8.50 | 7.83 |
| CW 95026 | 8.50 | 7.00 | 6.50 | 7.33 |
| CW 75046 | 7.50 | 6.50 | 6.50 | 6.83 |
| WinterGold | 5.00 | 6.00 | 4.75 | 5.25 |
| CW 83021 | 7.50 | 3.50 | 3.50 | 4.83 |
| CW 85029 | 7.00 | 4.50 | 3.00 | 4.83 |
| WL 342 | 5.50 | 4.00 | 4.50 | 4.67 |
| Ameristand 403T | 5.00 | 5.00 | 4.00 | 4.67 |
| Mountaineer | 5.00 | 4.00 | 4.75 | 4.58 |
| 54V54 | 5.50 | 4.00 | 4.00 | 4.50 |
| 54H69 (C) | 4.00 | 3.50 | 5.00 | 4.17 |
| WL 325HQ | 5.00 | 4.00 | 3.00 | 4.00 |
| Magnum IV | 4.00 | 3.50 | 4.50 | 4.00 |
| 5 Star | 5.00 | 1.50 | 4.25 | 3.58 |
| Vernal | 4.50 | 3.00 | 3.00 | 3.50 |
| Magnum V | 4.00 | 2.00 | 3.75 | 3.25 |
| Multiplier 3 | 4.00 | 1.50 | 3.25 | 2.92 |
| Geneva | 4.00 | 2.00 | 2.75 | 2.92 |
| Grand Mean | 5.03 | 3.84 | 4.56 | 4.48 |
| LSD (0.05) | 2.09 | 3.08 | 1.29 | 1.59 |
| C.V. (%) | 29.40 | 56.70 | 20.02 | 25.13 |
| R2 | 0.45 | 0.44 | 0.68 | 0.58 |

TABLE 7b

The standability of alfalfa varieties 'CW 95026', 'CW 75046', 'CW 83201', and 'CW 85029' as compared to commercially available check varieties all grown at the same time in the same location. A02WIWS - Spring Forage Yield Trial at West Salem, WI.

| Date Last Cut/Spring Greenup | August 2 |
|---|---|
| # days growing | 32 |
| Date Rated | Sep. 3, 2002 |

| Entry | Standability Ratings |
|---|---|
| CW 14032 | 8.00 |
| CW 15009 | 8.00 |
| Europe | 7.50 |
| CW 10090 | 6.75 |
| CW 15033 | 6.25 |
| CW 95026 | 6.25 |
| CW 10089 | 5.00 |
| CW 15041 | 4.75 |
| CW 75046 | 4.75 |
| CW 15030 | 4.25 |
| Ascend | 4.00 |
| CW 85029 | 3.75 |
| CW 15040 | 3.25 |
| CW 83021 | 3.25 |
| CW 14010 | 3.25 |
| CW 15008 | 3.00 |
| HybriForce-400 | 2.50 |
| Magnum IV | 1.75 |
| Sommerset | 1.50 |
| Geneva | 1.50 |
| Ameristand 403T | 1.50 |
| 54V54 | 1.25 |
| DK A42-15 | 1.00 |
| WL 319HQ | 1.00 |
| Vernal | 1.00 |

TABLE 7b-continued

The standability of alfalfa varieties 'CW 95026', 'CW 75046', 'CW 83201', and 'CW 85029' as compared to commercially available check varieties all grown at the same time in the same location. A02WIWS - Spring Forage Yield Trial at West Salem, WI.

| Grand Mean | 2.48 |
|---|---|
| LSD (0.05) | 1.28 |
| C.V. (%) | 36.36 |
| R2 | 0.85 |

TABLE 7c

The standability of alfalfa varieties 'CW 95026', 'CW 75046', 'CW 83201', and 'CW 85029' as compared to commercially available check varieties all grown at the same time in the same location. E99WIWS - Spring Forage Yield Trial at West Salem, WI.

| Date Last Cut/Spring Greenup | April 1 |
|---|---|
| # days growing | 53 |
| Date Rated | May 24 |

| Entry | Standability Ratings |
|---|---|
| Europe | 8.50 |
| CW 75046 | 6.50 |
| CW 75047 | 6.50 |
| Mercedes | 6.00 |
| CW 54040 = WinterGold | 3.00 |
| CW 85029 | 3.00 |
| CW 83021 | 2.50 |
| Grand Mean | 4.25 |
| LSD (0.05) | 1.31 |
| C.V. (%) | 21.73 |
| R2 | 0.82 |

TABLE 7d

The standability of alfalfa varieties 'CW 95026', 'CW 75046', 'CW 83201', and 'CW 85029' as compared to commercially available check varieties all grown at the same time in the same location. E01WIWS - Spring Forage Yield Trial at West Salem WI.

| Date Last Cut/Spring greenup | August 6 Year 1 | June 6 Year 2 | July 7 Year 2 | July 7 Year 2 | August 27 Year 2 | Average Year 2 |
|---|---|---|---|---|---|---|
| # days growing | 35 | 33 | 41 | 48 | 48 | 43 |
| Date Rated | September 10 | July 9 | August 20 | August 27 | October 14 | |

| Entry | Standability Ratings | | | | | |
|---|---|---|---|---|---|---|
| Europe | 8.50 | 7.00 | 8.50 | 8.50 | 9.00 | 8.25 |
| CW 04007 | 8.00 | 7.50 | 8.50 | 8.00 | 8.75 | 8.19 |
| CW 05008 | 7.50 | 6.50 | 7.50 | 8.50 | 8.75 | 7.81 |
| Marshall | 5.50 | 6.50 | 8.00 | 7.50 | 7.75 | 7.44 |
| Aubigny | 6.00 | 6.00 | 7.50 | 7.00 | 8.00 | 7.12 |
| Diane | 5.50 | 6.50 | 7.50 | 6.50 | 7.50 | 7.00 |
| Daisy | 6.50 | 6.50 | 7.00 | 7.50 | 6.75 | 6.94 |
| Mercedes | 6.00 | 5.00 | 6.50 | 8.00 | 7.50 | 6.75 |
| CW 95026 | 6.50 | 6.50 | 7.50 | 5.50 | 7.00 | 6.62 |
| CW 74000 | 6.50 | 6.00 | 6.50 | 6.50 | 7.50 | 6.62 |
| CW 95127 | 5.00 | 6.50 | 5.00 | 6.50 | 6.75 | 6.19 |
| CW 95125 | 4.50 | 6.00 | 6.00 | 5.50 | 6.00 | 5.88 |
| CW 75047 | 4.50 | 5.50 | 6.00 | 5.50 | 6.25 | 5.81 |
| CW 75046 | 5.00 | 3.50 | 6.50 | 5.00 | 6.25 | 5.31 |
| CW 95126 | 5.50 | 6.50 | 5.00 | 3.50 | 5.75 | 5.19 |
| CW 95124 | 5.00 | 6.00 | 4.50 | 4.50 | 5.75 | 5.19 |
| CW 95123 | 5.00 | 5.00 | 4.50 | 4.50 | 5.75 | 4.94 |
| CW 83021 | 5.00 | 4.00 | 4.50 | 2.50 | 4.00 | 3.75 |
| CW 85029 | 4.00 | 3.50 | 4.00 | 2.50 | 3.25 | 3.31 |
| Vernal | 2.50 | 3.50 | 5.00 | 3.00 | 1.50 | 3.25 |
| WinterGold | 2.50 | 3.00 | 3.00 | 2.50 | 4.00 | 3.13 |
| WL 325HQ | 0.50 | 4.00 | 2.50 | 1.50 | 2.75 | 2.69 |
| CW 92012 | 0.50 | 3.00 | 1.00 | 0.50 | 1.00 | 1.38 |

TABLE 7d-continued

The standability of alfalfa varieties 'CW 95026', 'CW 75046',
'CW 83201', and 'CW 85029' as compared to commercially available
check varieties all grown at the same time in the same location.
E01WIWS - Spring Forage Yield Trial at West Salem WI.

| | | | | | | |
|---|---|---|---|---|---|---|
| Grand Mean | 4.96 | 5.42 | 5.69 | 5.15 | 5.91 | 5.55 |
| LSD (0.05) | 1.10 | 1.99 | 1.49 | 1.45 | 1.13 | 0.84 |
| C.V. (%) | 15.73 | 26.01 | 18.54 | 19.88 | 13.56 | 10.67 |
| R2 | 0.90 | 0.58 | 0.82 | 0.87 | 0.91 | 0.93 |

TABLE 7e

Spring Forage Yield Trial at West Salem,. WI E01WIWS - Standability Notes.

| Date Last Cut/ Spring greenup # days growing Date Rated | August 6 Year 1 35 Sep. 19 | June 6 Year 2 33 July 9 | July 10 Year 2 41 August 20 | July 10 Year 2 48 August 27 | August 27 Year 2 48 October 14 | 43 Year 2 Ave. | April 14 Year 3 56 June 9 | June 9 Year 3 35 July 14 | 46 Year 3 Ave. | Years 1-3 Ave. |
|---|---|---|---|---|---|---|---|---|---|---|
| Entry | | | | | Standability | | | | | |
| Europe | 8.50 | 7.00 | 8.50 | 8.50 | 9.00 | 8.25 | 8.75 | 8.50 | 8.63 | 8.46 |
| CW 04007 | 8.00 | 7.50 | 8.50 | 8.00 | 8.75 | 8.19 | 9.00 | 5.75 | 7.38 | 7.85 |
| CW 05008 | 7.50 | 6.50 | 7.50 | 8.50 | 8.75 | 7.81 | 8.75 | 6.00 | 7.38 | 7.56 |
| Daisy | 6.50 | 6.50 | 7.00 | 7.50 | 6.75 | 6.94 | 8.75 | 6.50 | 7.63 | 7.02 |
| Marshal | 5.50 | 6.50 | 8.00 | 7.50 | 7.75 | 7.44 | 8.75 | 7.00 | 7.88 | 6.94 |
| Aubigny | 6.00 | 6.00 | 7.50 | 7.00 | 8.00 | 7.12 | 9.00 | 6.00 | 7.50 | 6.87 |
| CW 74000 | 6.50 | 6.00 | 6.50 | 6.50 | 7.50 | 6.62 | 9.00 | 5.50 | 7.25 | 6.79 |
| Mercedes | 6.00 | 5.00 | 6.50 | 8.00 | 7.50 | 6.75 | 8.75 | 5.75 | 7.25 | 6.67 |
| CW 95027 | 6.50 | 6.50 | 7.50 | 5.00 | 7.00 | 6.50 | 8.25 | 5.50 | 6.88 | 6.63 |
| Diane | 5.50 | 6.50 | 7.50 | 6.50 | 7.50 | 7.00 | 8.75 | 6.00 | 7.38 | 6.62 |
| CW 95026 | 6.50 | 6.50 | 7.50 | 5.50 | 7.00 | 6.62 | 8.25 | 4.50 | 6.38 | 6.50 |
| CW 95127 | 5.00 | 6.50 | 5.00 | 6.50 | 6.75 | 6.19 | 7.75 | 3.25 | 5.50 | 5.56 |
| CW 95125 | 4.50 | 6.00 | 6.00 | 5.50 | 6.00 | 5.88 | 7.75 | 2.75 | 5.25 | 5.21 |
| CW 75047 | 4.50 | 5.50 | 6.00 | 5.50 | 6.25 | 5.81 | 7.50 | 2.25 | 4.88 | 5.06 |
| CW 95126 | 5.50 | 6.50 | 5.00 | 3.50 | 5.75 | 5.19 | 6.75 | 2.00 | 4.38 | 5.02 |
| CW 95123 | 5.00 | 5.00 | 4.50 | 4.50 | 5.75 | 4.94 | 7.75 | 2.25 | 5.00 | 4.98 |
| CW 75046 | 5.00 | 3.50 | 6.50 | 5.00 | 6.25 | 5.31 | 7.00 | 2.25 | 4.63 | 4.98 |
| CW 95124 | 5.00 | 6.00 | 4.50 | 4.50 | 5.75 | 5.19 | 6.75 | 2.25 | 4.50 | 4.90 |
| CW 85047 | 4.50 | 5.00 | 4.00 | 3.50 | 5.25 | 4.44 | 7.75 | 3.00 | 5.38 | 4.77 |
| CW 83021 | 5.00 | 4.00 | 4.50 | 2.50 | 4.00 | 3.75 | 7.00 | 2.00 | 4.50 | 4.42 |
| CW 85029 | 4.00 | 3.50 | 4.00 | 2.50 | 3.25 | 3.31 | 6.75 | 1.75 | 4.25 | 3.85 |
| Vernal | 2.50 | 3.50 | 5.00 | 3.00 | 1.50 | 3.25 | 7.75 | 3.25 | 5.50 | 3.75 |
| CW 64010 | 2.00 | 5.50 | 4.00 | 4.50 | 4.00 | 4.50 | 7.00 | 2.25 | 4.63 | 3.71 |
| WinterGold | 2.50 | 3.00 | 3.00 | 2.50 | 4.00 | 3.13 | 7.75 | 2.00 | 4.88 | 3.50 |
| WL 325HQ | 0.50 | 4.00 | 2.50 | 1.50 | 2.75 | 2.69 | 5.25 | 1.50 | 3.38 | 2.19 |
| CW 92012 | 0.50 | 3.00 | 1.00 | 0.50 | 1.00 | 1.38 | 5.50 | 1.25 | 3.38 | 1.75 |
| Grand Mean | 4.96 | 5.42 | 5.69 | 5.15 | 5.91 | 5.55 | 7.77 | 3.88 | 5.83 | 5.44 |
| LSD (0.05) | 1.10 | 1.99 | 1.49 | 1.45 | 1.13 | 0.84 | 1.07 | 1.42 | 0.94 | 0.61 |
| C.V. (%) | 15.73 | 26.01 | 18.54 | 19.88 | 13.56 | 10.67 | 9.71 | 25.86 | 11.43 | 7.95 |
| R2 | 0.90 | 0.58 | 0.82 | 0.87 | 0.91 | 0.93 | 0.72 | 0.86 | 0.87 | 0.95 |

TABLE 7f

Spring Forage Yield Trial at Atlanta,
IN. A03INAT - Standability Notes.

| | Last Cut: Measured: # days: | July 9 August 12 34 | | |
|---|---|---|---|---|
| Entry | Rep. 1 | Rep. 2 | Rep. 3 | Standability |
| CW 14032 | 8.0 | 9.0 | 8.0 | 8.33 |
| CW 25039 | 8.0 | 9.0 | 4.0 | 7.00 |
| CW 95026 | 6.0 | 5.0 | 3.0 | 4.67 |
| CW 04023 | 4.0 | 5.0 | 3.0 | 4.00 |
| CW 15030 | 3.0 | 6.0 | 3.0 | 4.00 |
| CW 75046 | 5.0 | 4.0 | 3.0 | 4.00 |
| CW 15033 | 3.0 | 4.0 | 4.0 | 3.67 |
| CW 85029 | 3.0 | 4.0 | 4.0 | 3.67 |
| CW 83021 | 5.0 | 3.0 | 1.0 | 3.00 |
| WinterGold | 5.0 | 3.0 | 1.0 | 3.00 |
| Ameristand 403T | 1.0 | 4.0 | 3.0 | 2.67 |
| CW 25038 | 3.0 | 4.0 | 1.0 | 2.67 |
| TMF 421 | 5.0 | 1.0 | 1.0 | 2.33 |
| CW 24044 | 2.0 | 3.0 | 1.0 | 2.00 |
| Vernal | 4.0 | 1.0 | 1.0 | 2.00 |
| HybriForce-400 | 2.0 | 2.0 | 1.0 | 1.67 |
| 54V46 | 2.0 | 1.0 | 1.0 | 1.33 |
| HybriForce-420 Wet | 2.0 | 1.0 | 1.0 | 1.33 |
| WL 319HQ | 2.0 | 1.0 | 1.0 | 1.33 |
| Grand Mean | | | | 3.08 |
| LSD (0.05) | | | | 2.13 |
| C.V. (%) | | | | 42.48 |
| R2 | | | | 0.74 |

TABLE 7g

Spring Forage Yield Trial at West Salem, WI.
Q02WIWS Early Bloom 4c. Standability Notes.

| Last Cut: | | August 15 | | |
|---|---|---|---|---|
| Measured:<br># days: | | September 18<br>34 | | |
| Entry | Rep. 1 | Rep. 2 | Rep. 3 | Standability |
| Europe | 8 | 8 | 9 | 8.33 |
| CW 95026 | 6 | 4 | 9 | 6.33 |
| CW 75046 | 7 | 4 | 6 | 5.67 |
| CW 85029 | 5 | 4 | 4 | 4.33 |
| CW 83021 | 5 | 4 | 3 | 4.00 |
| HybriForce-400 | 5 | 4 | 3 | 4.00 |
| Vernal | 2 | 3 | 2 | 2.33 |
| WL 319HQ | 3 | 3 | 1 | 2.33 |
| Grand Mean | | | | 4.25 |
| LSD (0.05) | | | | 1.76 |
| C.V. (%) | | | | 25.41 |
| R2 | | | | 0.70 |

Example 3

Development of New Alfalfa Varieties

Alfalfa Variety 'CW 75046'

'CW 75046' is a high yielding, persistent variety with improved standability and fast recovery after spring green-up or after harvest with no observed soil type or management limitations. 'CW 75046' is a synthetic variety with 225 parent plants that were selected for resistance to *Phytophthora* root rot. Parent plants were selected from crosses between selections from two year old Wisconsin nurseries for winter survival, leaf disease resistance, healthy green color, fast recovery after spring green-up or after harvest, and high standability; and from crosses between the nursery selections and selections from three year old Wisconsin and Minnesota yield trials for moderate to late fall dormancy, good agronomic appearance, fast recovery, high leaf to stem ratio, and resistance to crown rot, Bacterial wilt, *Fusarium* wilt, and *Verticillium* wilt.

Alfalfa variety 'CW 75046' was developed by the following method:

In the initial step, 1,382 French lines (half-sib families or populations) were seeded into the field at West Salem, Wis. The resulting plants were selected after two years for winter hardiness, leaf disease resistance, high leaf to stem ratio, fast recovery after spring green-up or after harvest (rate of regrowth after harvest), high standability (>90% of stems were upright at 50% flowering or late bloom), and high yield potential. The initial French lines were derived by phenotypic recurrent selection for vigor, height, agronomic appearance, high standability and resistance to *Verticillium* wilt.

In step 2, 'CW 3408' ('Gold Plus') and 'CW 3512' ('512') were seeded (17 lbs/acre) into the field at Owatonna, Minn.; Manitowoc, Wis.; and West Salem, Wis. The resulting plants were selected after three years for moderate to late fall dormancy, good agronomic appearance, fast recovery, high leaf to stem ratio, multifoliolate leaf expression, and resistance to crown rot, Bacterial wilt, *Fusarium* wilt, and *Verticillium* wilt. 'Gold Plus' is a synthetic variety with 165 parent plants that were sequentially selected for multifoliate leaf expression and for resistance to *Phytophthora* root rot and *Aphanomyces* root rot (race 1). Parent plants were selected from a polycross among moderate fall dormant selections from three year-old Wisconsin yield trials. '512' is a synthetic variety with 180 parent plants which were sequentially selected for multifoliate leaf expression and for resistance to *Phytophthora* root rot and *Aphanomyces* root rot (race 1). Parent plants were selected from a polycross among late fall dormant selections from three year-old Pennsylvania yield trials.

In step 3, 77 of the highest standability plants from Step 1 were poly crossed (97-033).

In step 4, 34 of the most persistent Gold Plus plants from Step 2 were crossed as males (97-034) to the 77 French plants from Step 1.

In step 5, 34 of the most persistent 512 plants from Step 2 were crossed as males (97-035) to the 77 French plants from Step 1.

In step 6, a large number of seeds (2,800) resulting from cross 97-033 were planted and selected for resistance to *Aphanomyces* root rot and *Phytophthora* root rot.

In step 7, a large number of seeds (2,400) resulting from cross 97-034 were planted and selected for resistance to *Phytophthora* root rot.

In step 8, a large number of seeds (2,400) resulting from cross 97-035 were planted and selected for resistance to *Phytophthora* root rot.

In step 9, 225 of the most *Phytophthora* root rot resistant plants from Step 6 (15 plants), Step 7 (105 plants), and Step 8 (105 plants) were transplanted together under cage isolation. All 225 plants were crossed with one another in Step 9 using leafcutter bees, and Breeder seed (Synthetic Generation 1, or "Syn 1") was bulked from all seed from all 225 plants.

Breeder seed was produced under cage isolation near Woodland, Calif. Seed was bulk harvested from all parent plants.

Breeder seed (Syn. 1) was produced under cage isolation near Woodland, Calif. Cal/West Seeds will maintain sufficient foundation seed (Syn.2 or Syn.3) for the projected life of the variety. Production of Syn.3 foundation seed requires consent of the breeder.

The above method produced alfalfa variety 'CW 75046'. The primary uses of plants of the 'CW 75046' variety are for hay, haylage, greenchop, and dehydration. 'CW 75046' is adapted to the North Central, East Central, and Great Plains areas of the U.S. and is intended for use in the North Central, East Central, Great Plains, and moderately winter-hardy intermountain areas of the U.S. and in Canada. 'CW 75046' has been tested in California, Iowa, Nebraska, Pennsylvania, South Dakota, and Wisconsin.

'CW 75046' is a late dormant variety with fall dormancy similar to FD class 5 check varieties. Flower color observed in the Syn.2 generation is greater than 99% purple, with a trace of variegated, white, cream, and yellow. Flower color at full bloom for Syn. 2 generation is: 99% Purple; 1% Variegated; Trace % Cream; Trace % Yellow; Trace % White (See USDA Agriculture Handbook No. 424—A System for Visually Classifying Alfalfa Flower Color.).

TABLE 8

Selected characteristics of alfalfa variety 'CW 75046'

| Trait | Rating or Description |
|---|---|
| Fall Dormancy Rating | 5 |
| Winter Survival Rating | 2 |
| Recovery after Harvest Rating | 9% faster or 2.20 cm/day when compared to check variety WinterGold at 1.99 cm/day |
| Standability Rating | 5.31 |
| Multifoliolate Leaf Expression Rating | 84% |
| Multifoliolate Index | 2.57 when compared to check variety Proof at 3.35 |
| Field Appearance | At the bud stage, plants will be tall with an upright growth habit and the canopy will appear full and leafy |

TABLE 9

Yield Performance of 'CW 75046'.

| Location | Date Seeded | Relative Year | Harvest Years | Total Yield of CW 75046 (Tons/Acre) | Mean Yield of Trial (Tons/Acre) |
|---|---|---|---|---|---|
| West Salem, WI | May 12 | Year 1 | 3 | 17.86 | 13.87 |
| West Salem, WI | May 10 | Year 2 | 4 | 26.72 | 24.83 |
| Manitowoc, WI | April 30 | Year 3 | 2 | 7.81 | 8.26 |
| Rock Springs, PA | April 1 | Year 3 | 2 | 12.18 | 11.66 |
| West Salem, WI | April 26 | Year 3 | 2 | 11.25 | 11.38 |
| West Salem, WI | April 26 | Year 3 | 2 | 10.19 | 9.84 |
| West Salem, WI | April 17 | Year 4 | 1 | 3.92 | 4.02 |
| Lennox, SD | April 18 | Year 4 | 1 | 2.41 | 2.38 |
| Mead, NE | May 10 | Year 2 | 2 | 16.49 | 16.22 |
| Totals | | | 19 | 108.83 | 102.46 |

TABLE 10a

Forage Quality of 'CW 75046'. A01WIWS - Spring Forage Yield Trial at West Salem, WI.

| Entry | Total Yield DM tons/acre | CP | ADF | NDF | ADL | NDFD | Relative Forage Quality (RFQ) | Milk lbs/Ton | Milk lbs/Acre |
|---|---|---|---|---|---|---|---|---|---|
| CW 75046 | 5.56 | 22.42 | 28.09 | 34.30 | 5.58 | 47.54 | 204 | 3,029 | 16,831 |
| 54V54 | 5.63 | 22.22 | 28.08 | 34.39 | 5.54 | 47.84 | 205 | 3,048 | 17,173 |
| Ameristand 403T | 5.47 | 23.23 | 27.60 | 33.19 | 5.40 | 48.57 | 215 | 3,119 | 17,067 |
| Magnum V | 5.77 | 22.44 | 28.84 | 34.85 | 5.76 | 48.17 | 202 | 3,049 | 17,580 |
| Vernal | 4.71 | 21.67 | 28.47 | 34.66 | 5.51 | 48.69 | 206 | 3,085 | 14,534 |
| WinterGold | 5.50 | 23.21 | 25.78 | 31.47 | 4.99 | 48.81 | 230 | 3,200 | 17,590 |
| WL 325HQ | 5.51 | 23.04 | 27.62 | 33.46 | 5.38 | 47.90 | 211 | 3,075 | 16,929 |
| Trial Mean | 5.63 | 22.79 | 27.46 | 33.32 | 5.37 | 48.35 | 215 | 3,105 | 17,467 |
| LSD (0.05) | 0.46 | 0.79 | 1.50 | 1.70 | 0.36 | 0.88 | 11.80 | 75.62 | 1,303.70 |
| C.V. (%) | 5.81 | 2.45 | 3.87 | 3.61 | 4.71 | 1.29 | 3.88 | 1.72 | 5.28 |
| R2 | 0.77 | 0.61 | 0.51 | 0.55 | 0.56 | 0.51 | 0.64 | 0.53 | 0.77 |

TABLE 10b

Forage Quality of 'CW 75046'. E01WIWS - Spring Forage Yield Trial at West Salem, WI.

| Entry | Total Yield DM tons/acre | CP | ADF | NDF | ADL | NDFD | Relative Forage Quality (RFQ) | Milk lbs/Ton | Milk lbs/Acre |
|---|---|---|---|---|---|---|---|---|---|
| CW 75046 | 6.73 | 19.81 | 36.49 | 44.01 | 7.74 | 43.55 | 137.19 | 2,584.12 | 17,401.29 |
| Europe | 6.29 | 19.28 | 36.10 | 43.81 | 7.67 | 43.45 | 138.00 | 2,600.16 | 16,362.71 |
| Vernal | 5.57 | 19.02 | 36.90 | 44.49 | 7.72 | 44.55 | 137.97 | 2,604.67 | 14,496.89 |
| WinterGold | 6.59 | 20.04 | 34.74 | 42.23 | 7.39 | 44.81 | 148.92 | 2,706.82 | 17,852.38 |
| WL 325HQ | 6.47 | 20.49 | 34.72 | 42.09 | 7.21 | 44.49 | 148.51 | 2,679.75 | 17,333.97 |
| Trial Mean | 6.51 | 19.58 | 35.89 | 43.51 | 7.58 | 44.26 | 141.74 | 2,631.92 | 17,134.80 |
| LSD (0.05) | 0.25 | 1.08 | 1.99 | 2.43 | 0.51 | 0.65 | 11.90 | 97.93 | 928.95 |
| C.V. (%) | 2.76 | 3.90 | 3.92 | 3.95 | 4.74 | 1.03 | 5.93 | 2.63 | 3.83 |
| R2 | 0.90 | 0.54 | 0.37 | 0.33 | 0.31 | 0.62 | 0.33 | 0.35 | 0.84 |

TABLE 11a

Disease Resistance of 'CW 75046'.

| Disease | Level of Resistance |
|---|---|
| Anthracnose | R |
| *Aphanomyces* Root Rot | R |
| Bacterial Wilt | HR |
| *Fusarium* Wilt | HR |
| *Phytophthora* Root Rot | R |
| *Verticillium* Wilt | R |

TABLE 11b

Insect Resistance of 'CW 75046'.

| Insect | Level of Resistance |
|---|---|
| Pea Aphid | R |
| Spotted Alfalfa Aphid | R |

TABLE 11c

Nematode Resistance of 'CW 75046'.

| Nematode | Level of Resistance |
|---|---|
| Stem | MR |
| Northern Root Knot | LR |

Alfalfa Variety 'CW 83201'

'CW 83201' is a high yielding, persistent alfalfa variety with improved standability and fast recovery after harvest with no observed soil type or management limitations. 'CW 83201' is a synthetic variety with 225 parent plants that were selected sequentially for multifoliate leaf expression and for resistance to *Phytophthora* root. Parent plants were selected from crosses between selections from three year old Wisconsin nurseries for winter survival, leaf disease resistance, healthy green color, fast recovery after harvest, and high standability; and from crosses between the nursery selections and selections from three year old Wisconsin and Minnesota yield trials for moderate fall dormancy, good agronomic appearance, fast recovery, high leaf to stem ratio, resistance to crown rot, Bacterial wilt, *Fusarium* wilt, and *Verticillium* wilt.

In the initial step, 1,382 French lines (half-sib families or populations) were seeded into the field at West Salem, Wis. The resulting plants were selected after three years for winter hardiness, leaf disease resistance, high leaf to stem ratio, fast recovery after harvest (rate of regrowth after harvest), high standability (>90% of stems were upright at 50% flowering or late bloom), and high forage yield potential. The initial French lines were derived by phenotypic recurrent selection for vigor, height, agronomic appearance, high standability and resistance to *Verticillium* wilt.

In step 2, 864 elite alfalfa clones from elite populations adapted to North America were transplanted in the field at West Salem, Wis. The resulting plants were selected after three years for winter survival, leaf disease resistance, high leaf to stem ratio, fast recovery after harvest (rate of regrowth after harvest), high forage yield, high relative feed value (using Near Infrared Reflectance Spectroscopy or NIRS), moderate fall dormancy, good agronomic appearance, crown rot resistance, Bacterial wilt resistance, *Fusarium* wilt resistance, and *Verticillium* wilt resistance.

In step 3, 9504 alfalfa plants from elite populations adapted to North America were selected for resistance to *Phytophthora* root rot, *Aphanomyces* root rot (race 1), and anthracnose (Race 1) and then inoculated with bacterial wilt, *Fusarium* wilt and *Verticillium* wilt and transplanted in the field at West Salem, Wis. The resulting plants were selected after three years for winter survival, leaf disease resistance, high leaf to stem ratio, fast recovery after harvest (rate of regrowth after harvest), high forage yield, high relative feed value (using Near Infrared Reflectance Spectroscopy, moderate fall dormancy, good agronomic appearance, crown rot resistance, Bacterial wilt resistance, *Fusarium* wilt resistance, and *Verticillium* wilt resistance.

In step 4, numerous elite alfalfa populations were seeded (17 lbs/acre) into the field at Owatonna, Minn.; Madison, Wis.; Prescott, Wis.; and West Salem, Wis. The resulting plants were selected after three years for moderate fall dormancy, good agronomic appearance, fast recovery, high leaf to stem ratio, resistance to crown rot, Bacterial wilt, *Fusarium* wilt, and *Verticillium* wilt.

In step 5, 35 of the highest standability plants from Step 1 were poly crossed (98-031).

In step 6, 32 of the fastest recovery alfalfa clones from Step 2 and 23 of the fastest recovery alfalfa plants from Step 3 were crossed as males (98-032) to the 35 French plants from Step 1.

In step 7, 173 of the fastest recovery alfalfa plants from Step 4 were crossed as males (98-033) to the 35 French plants from Step 1.

In step 8, a large number of seeds (2,400) resulting from cross 98-031 were planted and selected for resistance to *Phytophthora* root rot.

In step 9, a large number of seeds (1,200) resulting from cross 98-032 were planted and selected for resistance to *Phytophthora* root rot.

In step 10, a large number of seeds (1,200) resulting from cross 98-033 were planted and selected for resistance to *Phytophthora* root rot.

In step 11, 225 of the most *Phytophthora* root rot resistant plants from Step 8 (75 plants), Step 9 (75 plants), and Step 10 (75 plants) were transplanted together under cage isolation. All 225 plants were crossed with one another in Step 11 using leaf cutter bees, and Breeder seed (Synthetic Generation 1, or "Syn 1") was bulked from all seed from all 225 plants.

Breeder seed was produced under cage isolation near Woodland, Calif. Seed was bulk harvested from all parent plants.

Breeder seed (Syn.1) was produced under cage isolation near Woodland, Calif. Cal/West Seeds will maintain sufficient foundation seed (Syn.2 or Syn.3) for the projected life of the variety. Production of Syn.3 foundation seed requires consent of the breeder.

The above method produced alfalfa variety 'CW 83201'. The primary uses of plants of the 'CW 83201' variety are for hay, haylage, greenchop, and dehydration. 'CW 83201' is adapted to the North Central, East Central, and Great Plains areas of the U.S. and is intended for use in the North Central, East Central, Great Plains, and moderately winter-hardy intermountain areas of the U.S. and in Canada. 'CW 83201' has been tested in California, Nebraska, Pennsylvania, South Dakota, and Wisconsin.

'CW 83201' is a moderate dormant variety with fall dormancy similar to FD class 4 check varieties. Flower color observed in the Syn.2 generation is approximately: greater than 99% purple, with a trace of variegated, white, cream, and yellow (See USDA Agriculture Handbook No. 424—A System for Visually Classifying Alfalfa Flower Color.).

'CW 83201' has high resistance to *Fusarium* wilt and resistance to anthracnose (race 1), bacterial wilt, *Verticillium* wilt, *Phytophthora* root rot, *Aphanomyces* root rot (race 1).

TABLE 12

Selected characteristics of Alfalfa Variety 'CW 83201'

| Trait | Rating or Description |
|---|---|
| Fall Dormancy Rating | 4 |
| Winter Survival Rating | 2 |
| Recovery after Harvest Rating | 30% faster or 2.57 cm/day when compared to check variety WinterGold at 1.99 cm/day |
| Standability Rating | 3.75 |
| Multifoliolate Leaf Expression Rating | 66% |
| Multifoliolate Index | 2.27 when compared to check variety Proof at 3.35 |
| Field Appearance | At the bud stage, plants will be tall with an upright growth habit and the canopy will appear full and leafy |

TABLE 13

Yield Performance of alfalfa variety 'CW 83201'.

| Location | Date Seeded | Year | Harvest Years | Total Yield of CW 83021 (Tons/Acre) | Mean Yield of Trial (Tons/Acre) |
|---|---|---|---|---|---|
| West Salem, WI | May 10 | 1 | 4 | 29.34 | 24.83 |
| Manitowoc, WI | April 30 | 2 | 2 | 8.58 | 8.26 |
| Rock Springs, PA | April 1 | 2 | 2 | 10.88 | 11.66 |
| West Salem, WI | April 26 | 2 | 2 | 11.82 | 11.38 |
| West Salem, WI | April 26 | 2 | 2 | 9.98 | 9.84 |
| West Salem, WI | April 17 | 3 | 1 | 3.68 | 4.02 |
| Lennox, SD | April 18 | 3 | 1 | 2.17 | 2.38 |
| Mead, NE | May 10 | 2 | 2 | 16.06 | 16.22 |
| Totals | | | 16 | 92.51 | 88.59 |

TABLE 14a

Forage Quality of alfalfa variety 'CW 83201'. A01WIWS - Spring Forage Yield Trial at West Salem, WI.

| Entry | Total Yield DM tons/acre | CP | ADF | NDF | ADL | NDFD | Relative Forage Quality (RFQ) | Milk lbs/Ton | Milk lbs./Acre |
|---|---|---|---|---|---|---|---|---|---|
| CW 83021 | 6.16 | 20.84 | 30.12 | 36.82 | 6.00 | 47.51 | 191 | 2,981 | 18,325 |
| 54V54 | 5.63 | 22.22 | 28.08 | 34.39 | 5.54 | 47.84 | 205 | 3,048 | 17,173 |
| Ameristand 403T | 5.47 | 23.23 | 27.60 | 33.19 | 5.40 | 48.57 | 215 | 3,119 | 17,067 |
| Magnum V | 5.77 | 22.44 | 28.84 | 34.85 | 5.76 | 48.17 | 202 | 3,049 | 17,580 |
| Vernal | 4.71 | 21.67 | 28.47 | 34.66 | 5.51 | 48.69 | 206 | 3,085 | 14,534 |
| WinterGold | 5.50 | 23.21 | 25.78 | 31.47 | 4.99 | 48.81 | 230 | 3,200 | 17,590 |
| WL 325HQ | 5.51 | 23.04 | 27.62 | 33.46 | 5.38 | 47.90 | 211 | 3,075 | 16,929 |
| Trial Mean | 5.63 | 22.79 | 27.46 | 33.32 | 5.37 | 48.35 | 215 | 3,105 | 17,467 |
| LSD (0.05) | 0.46 | 0.79 | 1.50 | 1.70 | 0.36 | 0.88 | 11.80 | 75.62 | 1,303.70 |
| C.V. (%) | 5.81 | 2.45 | 3.87 | 3.61 | 4.71 | 1.29 | 3.88 | 1.72 | 5.28 |
| R2 | 0.77 | 0.61 | 0.51 | 0.55 | 0.56 | 0.51 | 0.64 | 0.53 | 0.77 |

TABLE 14b

Forage Quality of alfalfa variety 'CW 83201'.
E01WIWS - Spring Forage Yield Trial at West Salem, WI.

| Entry | Total Yield DM tons/acre | CP | ADF | NDF | ADL | NDFD | Relative Forage Quality (RFQ) | Milk lbs/Ton | Milk lbs./Acre |
|---|---|---|---|---|---|---|---|---|---|
| CW 83021 | 7.00 | 19.18 | 36.34 | 43.98 | 7.66 | 44.23 | 140.31 | 2,615.85 | 18,313.50 |
| Europe | 6.29 | 19.28 | 36.10 | 43.81 | 7.67 | 43.45 | 138.00 | 2,600.16 | 16,362.71 |
| Vernal | 5.57 | 19.02 | 36.90 | 44.49 | 7.72 | 44.55 | 137.97 | 2,604.67 | 14,496.89 |
| WinterGold | 6.59 | 20.04 | 34.74 | 42.23 | 7.39 | 44.81 | 148.92 | 2,706.82 | 17,852.38 |
| WL 325HQ | 6.47 | 20.49 | 34.72 | 42.09 | 7.21 | 44.49 | 148.51 | 2,679.75 | 17,333.97 |
| Trial Mean | 6.51 | 19.58 | 35.89 | 43.51 | 7.58 | 44.26 | 141.74 | 2,631.92 | 17,134.80 |
| LSD (0.05) | 0.25 | 1.08 | 1.99 | 2.43 | 0.51 | 0.65 | 11.90 | 97.93 | 928.95 |
| C.V. (%) | 2.76 | 3.90 | 3.92 | 3.95 | 4.74 | 1.03 | 5.93 | 2.63 | 3.83 |
| R2 | 0.90 | 0.54 | 0.37 | 0.33 | 0.31 | 0.62 | 0.33 | 0.35 | 0.84 |

TABLE 15a

Disease Resistance of alfalfa variety 'CW 83201'.

| Disease | Level of Resistance |
| --- | --- |
| Anthracnose | R |
| *Aphanomyces* Root Rot | R |
| Bacterial Wilt | R |
| *Fusarium* Wilt | HR |
| *Phytophthora* Root Rot | R |
| *Verticillium* Wilt | R |

TABLE 15b

Insect Resistance of alfalfa variety 'CW 83201'.

| Insect | Level of Resistance |
| --- | --- |
| Pea Aphid | R |
| Spotted Alfalfa Aphid | R |

TABLE 15c

Nematode Resistance of alfalfa variety 'CW 83201'.

| Nematode | Level of Resistance |
| --- | --- |
| Stem | MR |
| Northern Root Knot | LR |

Alfalfa Variety 'CW 85029'.

'CW 85029' is a synthetic variety with 225 parent plants that were selected sequentially for multifoliate leaf expression and for resistance to *Phytophthora* root. Parent plants were selected from crosses between selections from three year old Wisconsin nurseries for winter survival, leaf disease resistance, healthy green color, fast recovery after harvest, and high standability; and from crosses between the nursery selections and selections from three year old Wisconsin and Minnesota yield trials for moderate to late fall dormancy, good agronomic appearance, fast recovery, high leaf to stem ratio, resistance to crown rot, Bacterial wilt, *Fusarium* wilt, and *Verticillium* wilt.

In the initial step, 1,382 French lines (half-sib families or populations) were seeded into the field at West Salem, Wis. The resulting plants were selected after three years for winter hardiness, leaf disease resistance, high leaf to stem ratio, fast recovery after harvest (rate of regrowth after harvest), high standability (>90% of stems were upright at 50% flowering or late bloom), moderate to late fall dormancy, and high forage yield potential. The initial French lines were derived by phenotypic recurrent selection for vigor, height, agronomic appearance, high standability and resistance to *Verticillium* wilt.

In step 2, 864 elite alfalfa clones from elite populations adapted to North America were transplanted in the field at West Salem, Wis. The resulting plants were selected after three years for winter survival, leaf disease resistance, high leaf to stem ratio, fast recovery after harvest (rate of regrowth after harvest), high forage yield, high relative feed value (using Near Infrared Reflectance Spectroscopy), moderate to late fall dormancy, good agronomic appearance, crown rot resistance, Bacterial wilt resistance, *Fusarium* wilt resistance, and *Verticillium* wilt resistance.

In step 3, 9504 alfalfa plants from elite populations adapted to North America were selected for resistance to *Phytophthora* root rot, *Aphanomyces* root rot (race 1), and anthracnose (Race 1) and then inoculated with bacterial wilt, *Fusarium* wilt and *Verticillium* wilt and transplanted in the field at West Salem, Wis. The resulting plants were selected after three years for winter survival, leaf disease resistance, high leaf to stem ratio, fast recovery after harvest (rate of regrowth after harvest), high forage yield, high relative feed value (using Near Infrared Reflectance Spectroscopy), moderate to late fall dormancy, good agronomic appearance, crown rot resistance, Bacterial wilt resistance, *Fusarium* wilt resistance, and *Verticillium* wilt resistance.

In step 4, Numerous elite alfalfa populations were seeded (17 lbs/acre) into the field at Owatonna, Minn., Madison, Wis., and Prescott, Wis. The resulting plants were selected after three years for moderate to late fall dormancy, good agronomic appearance, fast recovery, high leaf to stem ratio, resistance to crown rot, Bacterial wilt, *Fusarium* wilt, and *Verticillium* wilt.

In step 5, 45 of the highest standability plants from Step 1 were poly crossed (98-053).

In step 6, 20 of the fastest recovery alfalfa clones from Step 2 and 18 of the fastest recovery alfalfa plants from Step 3 were crossed as males (98-054) to the 45 French plants from Step 1.

In step 7, 87 of the fastest recovery alfalfa plants from Step 4 were crossed as males (98-055) to the 45 French plants from Step 1.

In step 8, a large number of seeds (2,400) resulting from cross 98-053 were planted and selected for resistance to *Phytophthora* root rot.

In step 9, a large number of seeds (1,200) resulting from cross 98-054 were planted and selected for resistance to *Phytophthora* root rot.

In step 10, a large number of seeds (1,200) resulting from cross 98-055 were planted and selected for resistance to *Phytophthora* root rot.

In step 11, 225 of the most *Phytophthora* root rot resistant plants from Step 8 (75 plants), Step 9 (75 plants), and Step 10 (75 plants) were transplanted together under cage isolation. All 225 plants were crossed with one another in Step 11 using leaf cutter bees, and Breeder seed (Synthetic Generation 1, or "Syn 1") was bulked from all seed from all 225 plants.

Breeder seed was produced under cage isolation near Woodland, Calif. Seed was bulk harvested from all parent plants.

Breeder seed (Syn.1) was produced under cage isolation near Woodland, Calif.

The primary uses of plants of the 'CW 85029' variety are for hay, haylage, greenchop, and dehydration. 'CW 85029' is adapted to the North Central, East Central, and Great Plains areas of the U.S. and is intended for use in the North Central, East Central, Great Plains, and moderately winter-hardy intermountain areas of the U.S. and in Canada.

'CW 85029' has been tested in California, Nebraska, Pennsylvania, South Dakota, Wisconsin, and Washington.

'CW 85029' is a moderate dormant variety with fall dormancy similar to FD class 4 check varieties. Flower color observed in the Syn.2 generation is approximately: approximately 98% purple; 1% variegated; 1% white; with a trace of cream and yellow (See USDA Agriculture Handbook No. 424—A System for Visually Classifying Alfalfa Flower Color.).

'CW 85029' has high resistance to Bacterial wilt, *Fusarium* wilt, and *Phytophthora* root rot, resistance to anthracnose (race 1) and *Verticillium* wilt and moderate resistance to *Aphanomyces* root rot (race 1).

TABLE 16 selected characteristics of alfalfa variety 'CW 85029'.

| Trait | Rating or Description |
|---|---|
| Fall Dormancy Rating | 4 |
| Winter Survival Rating | 2 |
| Recovery after Harvest Rating | 30% faster or 2.62 cm/day when compared to check variety WinterGold at 1.99 cm/day |
| Standability Rating | 3.31 |
| Multifoliolate Leaf Expression Rating | 52% |
| Multifoliolate Index | 2.02 when compared to check variety Proof at 3.35 |
| Field Appearance | At the bud stage, plants will be tall with a full, dense canopy. Medium dark green plant color |

TABLE 17

Yield Performance of 'CW 85029'.

| Location | Date Seeded | Year | Harvest Years | Total Yield of CW 85029 (Tons/Acre) | Mean Yield of Trial (Tons/Acre) |
|---|---|---|---|---|---|
| West Salem, WI | May 10 | 1 | 4 | 28.70 | 24.83 |
| Basin City, WA | April 21 | 1 | 3 | 13.80 | 13.76 |
| Manitowoc, WI | April 30 | 2 | 2 | 8.16 | 8.26 |
| Rock Springs, PA | April 01 | 2 | 2 | 11.66 | 11.66 |
| West Salem, WI | April 26 | 2 | 2 | 11.69 | 11.38 |
| West Salem, WI | April 26 | 2 | 2 | 9.70 | 9.84 |
| West Salem, WI | April 17 | 3 | 1 | 3.99 | 4.02 |
| Lennox, SD | April 18 | 3 | 1 | 2.41 | 2.38 |
| Mead, NE | May 10 | 2 | 2 | 16.68 | 16.22 |
| Totals | | | 19 | 106.79 | 102.35 |

TABLE 19a

Disease Resistance of 'CW 85029'.

| Disease | Level of Resistance |
|---|---|
| Anthracnose | R |
| *Aphanomyces* Root Rot | MR |
| Bacterial Wilt | HR |
| *Fusarium* Wilt | HR |
| *Phytophthora* Root Rot | HR |
| *Verticillium* Wilt | R |

TABLE 19b

Insect Resistance. of 'CW 85029'.

| Insect | Level of Resistance |
|---|---|
| Pea Aphid | R |
| Spotted Alfalfa Aphid | R |

TABLE 19c

Nematode Resistance of 'CW 85029'.

| Nematode | Level of Resistance |
|---|---|
| Stem | MR |
| Northern Root Knot | LR |

TABLE 18a

Forage Quality of 'CW 85029'. A01WIWS - Spring Forage Yield Trial at West Salem, WI.

| Entry | Total Yield DM tons/acre | CP | ADF | NDF | ADL | NDFD | Relative Forage Quality (RFQ) | Milk lbs/Ton | Milk lbs./Acre |
|---|---|---|---|---|---|---|---|---|---|
| CW 85029 | 6.01 | 21.30 | 29.29 | 35.54 | 5.82 | 47.50 | 199 | 3,045 | 18,291 |
| 54V54 | 5.63 | 22.22 | 28.08 | 34.39 | 5.54 | 47.84 | 205 | 3,048 | 17,173 |
| Ameristand 403T | 5.47 | 23.23 | 27.60 | 33.19 | 5.40 | 48.57 | 215 | 3,119 | 17,067 |
| Magnum V | 5.77 | 22.44 | 28.84 | 34.85 | 5.76 | 48.17 | 202 | 3,049 | 17,580 |
| Vernal | 4.71 | 21.67 | 28.47 | 34.66 | 5.51 | 48.69 | 206 | 3,085 | 14,534 |
| WinterGold | 5.50 | 23.21 | 25.78 | 31.47 | 4.99 | 48.81 | 230 | 3,200 | 17,590 |
| WL 325HQ | 5.51 | 23.04 | 27.62 | 33.46 | 5.38 | 47.90 | 211 | 3,075 | 16,929 |
| Trial Mean | 5.63 | 22.79 | 27.46 | 33.32 | 5.37 | 48.35 | 215 | 3,105 | 17,467 |
| LSD (0.05) | 0.46 | 0.79 | 1.50 | 1.70 | 0.36 | 0.88 | 11.80 | 75.62 | 1,303.70 |
| C.V. (%) | 5.81 | 2.45 | 3.87 | 3.61 | 4.71 | 1.29 | 3.88 | 1.72 | 5.28 |
| R2 | 0.77 | 0.61 | 0.51 | 0.55 | 0.56 | 0.51 | 0.64 | 0.53 | 0.77 |

TABLE 18b

Forage Quality of 'CW 85029'. E01WIWS - Spring Forage Yield Trial at West Salem, WI.

| Entry | Total Yield DM tons/acre | CP | ADF | NDF | ADL | NDFD | Relative Forage Quality (RFQ) | Milk lbs/Ton | Milk lbs./Acre |
|---|---|---|---|---|---|---|---|---|---|
| CW 85029 | 6.81 | 18.58 | 36.72 | 44.63 | 7.75 | 44.43 | 138.15 | 2,614.13 | 17,803.29 |
| Europe | 6.29 | 19.28 | 36.10 | 43.81 | 7.67 | 43.45 | 138.00 | 2,600.16 | 16,362.71 |
| Vernal | 5.57 | 19.02 | 36.90 | 44.49 | 7.72 | 44.55 | 137.97 | 2,604.67 | 14,496.89 |
| WinterGold | 6.59 | 20.04 | 34.74 | 42.23 | 7.39 | 44.81 | 148.92 | 2,706.82 | 17,852.38 |
| WL 325HQ | 6.47 | 20.49 | 34.72 | 42.09 | 7.21 | 44.49 | 148.51 | 2,679.75 | 17,333.97 |
| Trial Mean | 6.51 | 19.58 | 35.89 | 43.51 | 7.58 | 44.26 | 141.74 | 2,631.92 | 17,134.80 |
| LSD (0.05) | 0.25 | 1.08 | 1.99 | 2.43 | 0.51 | 0.65 | 11.90 | 97.93 | 928.95 |
| C.V. (%) | 2.76 | 3.90 | 3.92 | 3.95 | 4.74 | 1.03 | 5.93 | 2.63 | 3.83 |
| R2 | 0.90 | 0.54 | 0.37 | 0.33 | 0.31 | 0.62 | 0.33 | 0.35 | 0.84 |

Alfalfa Variety 'CW 95026'

'CW 95026' is a high yielding, persistent variety with improved standability and fast recovery after harvest with no observed soil type or management limitations. 'CW 95026' is a synthetic variety with 225 parent plants that were selected sequentially for resistance to *Phytophthora* root rot and anthracnose (race 1). Parent plants were selected from crosses between selections from two year old Wisconsin nurseries for winter survival, leaf disease resistance, healthy dark green color, fast recovery after harvest, and high standability; and from crosses between the nursery selections and selections from a three year old Wisconsin yield trial for moderate to late fall dormancy, good agronomic appearance, high leaf to stem ratio, fast recovery, high standability, resistance to crown rot, Bacterial wilt, *Fusarium* wilt, and *Verticillium* wilt.

In the initial step, 25 elite alfalfa clones from French selected for improved adaptation to North America were transplanted in the field at West Salem, Wis. The resulting plants were selected after two years for winter survival, leaf disease resistance, high leaf to stem ratio, fast recovery after harvest (rate of regrowth after harvest), high standability (>90% of stems were upright at 50% flowering or late bloom), high forage yield, high relative feed value (using Near Infrared Reflectance Spectroscopy), late fall dormancy, good agronomic appearance, crown rot resistance, Bacterial wilt resistance, *Fusarium* wilt resistance, and *Verticillium* wilt resistance. The initial French lines were derived by phenotypic recurrent selection for vigor, height, agronomic appearance, high standability and resistance to *Verticillium* wilt.

In step 2, 2159 alfalfa plants from elite populations adapted to North America and French populations improved for adaptation to North America are selected for resistance to *Phytophthora* root rot and anthracnose (Race 1) and then inoculated with *Verticillium* wilt and transplanted in the field at West Salem, Wis. The resulting plants are selected after two years for winter survival, leaf disease resistance, high leaf to stem ratio, fast recovery after harvest (rate of regrowth after harvest), high standability (>90% of stems were upright at 50% flowering or late bloom), high forage yield, high relative feed value (using Near Infrared Reflectance Spectroscopy), late fall dormancy, good agronomic appearance, crown rot resistance, Bacterial wilt resistance, *Fusarium* wilt resistance, and *Verticillium* wilt resistance. The initial French lines were derived by phenotypic recurrent selection for vigor, height, agronomic appearance, high standability and resistance to *Verticillium* wilt.

In step 3, CW 54010 experimental alfalfa variety is seeded (17 lbs/acre) into the field at West Salem, Wis. The resulting plants are selected after three years for moderate to late fall dormancy, good agronomic appearance, fast recovery, high standability, high leaf to stem ratio, multifoliolate leaf expression, resistance to crown rot, Bacterial wilt, *Fusarium* wilt, and *Verticillium* wilt. CW 54010 is a synthetic variety with 196 parent plants that were sequentially selected for multifoliate leaf expression and for resistance to *Phytophthora* root rot and *Aphanomyces* root rot (race 1). Parent plants were selected from a polycross among moderate fall dormant selections from three year-old Wisconsin nurseries for improved standability.

In step 4, 4 of the highest standability French alfalfa clones from Step 1 and 15 of the highest standability plants from Step 2 were poly crossed (99-038).

In step 5, 31 of the highest standability CW 54010 plants from Step 3 are poly crossed (99-039).

In step 6, 4 of the highest standability French clones from Step 1, 15 of the highest standability plants from Step 2, and 31 of the highest standability CW 54010 plants from Step 3 were polycrossed (99-041).

In step 7, a large number of seeds (2,400) resulting from cross 99-038 were planted and selected for resistance to *Phytophthora* root rot and anthracnose (race 1).

In step 8, a large number of seeds (1,200) resulting from cross 99-039 were planted and selected for resistance to *Phytophthora* root rot and anthracnose (race 1).

In step 9, a large number of seeds (1,200) resulting from cross 99-041 were planted and selected for resistance to *Phytophthora* root rot and anthracnose (race 1).

In step 10, 225 of the most *Phytophthora* root rot resistant plants from Step 7 (125 plants), Step 8 (50 plants), and Step 9 (50 plants) were transplanted together under cage isolation. All 225 plants were crossed with one another in Step 10 using leaf cutter bees, and Breeder seed (Synthetic Generation 1, or "Syn 1") was bulked from all seed from all 225 plants.

Breeder seed was produced under cage isolation near Woodland, Calif. Seed was bulk harvested from all parent plants.

Breeder seed (Syn.1) was produced under cage isolation near Woodland, Calif. in 1999. Cal/West Seeds will maintain sufficient foundation seed (Syn.2 or Syn.3) for the projected life of the variety. Production of Syn.3 foundation seed requires consent of the breeder.

The foregoing method produces plants of variety 'CW 95026'. The primary uses of plants of the 'CW 95026' variety are for hay, haylage, greenchop, and dehydration. 'CW 95026' is adapted to the North Central, East Central, and Great Plains areas of the U.S. and is intended for use in the North Central, East Central, Great Plains, and moderately winter-hardy intermountain areas of the U.S. and in Canada. 'CW 95026' has been tested in California, Iowa, Nebraska, Minnesota, Pennsylvania, South Dakota, and Wisconsin.

'CW 95026' is a late dormant variety with fall dormancy similar to FD class 5 check varieties. Flower color observed in the Syn.2 generation is approximately 99% purple, 1% white, with a trace of variegated, cream, and yellow (See USDA Agriculture Handbook No. 424—A System for Visually Classifying Alfalfa Flower Color.).

'CW 95026' has high resistance to anthracnose (race 1), *Aphanomyces* root rot (race 1). Bacterial wilt, *Fusarium* wilt, *Phytophthora* root rot and resistance to *Verticillium* wilt.

TABLE 20 selected characteristics of alfalfa variety 'CW 95026'.

| Trait | Rating or Description |
|---|---|
| Fall Dormancy Rating | 5 |
| Winter Survival Rating | 3 |
| Recovery after Harvest Rating | 21% faster or 2.36 cm/day when compared to check variety WinterGold at 1.99 cm/day |
| Standability Rating | 6.62 |
| Multifoliolate Leaf Expression Rating | 65% |
| Multifoliolate Index | 2.58 when compared to check variety Proof at 3.35 |
| Field Appearance | At the bud stage, plants will be tall with an upright growth habit and dense, uniform canopy. Medium dark green plant color. |

TABLE 21

Yield Performance of 'CW 95026'.

| Location | Date Seeded | Year | Harvest Years | Total Yield of CW 95026 (Tons/Acre) | Mean Yield of Trial (Tons/Acre) |
|---|---|---|---|---|---|
| Manitowoc, WI | April 30 | 2 | 2 | 8.46 | 8.26 |
| Davenport, IA | May 04 | 1 | 3 | 16.50 | 16.77 |
| Sauk Center, MN | May 19 | 1 | 3 | 8.43 | 8.09 |
| Newton, WI | May 3 | 1 | 3 | 15.78 | 15.01 |
| West Salem, WI | April 14 | 1 | 3 | 19.06 | 17.56 |
| Rock Springs, PA | April 1 | 2 | 2 | 11.57 | 11.66 |
| West Salem, WI | April 26 | 2 | 2 | 12.12 | 11.38 |
| West Salem, WI | April 26 | 2 | 2 | 10.09 | 9.84 |
| West Salem, WI | April 17 | 3 | 1 | 4.03 | 4.02 |
| Lennox, SD | April 18 | 3 | 1 | 2.22 | 2.38 |
| Mead, NE | May 10 | 2 | 2 | 15.77 | 16.22 |
| Totals | | | 24 | 124.03 | 121.19 |

TABLE 22a

Forage Quality of 'CW 95026'. A01WIWS - Spring Forage Yield Trial at West Salem, WI.

| Entry | Total Yield DM tons/acre | CP | ADF | NDF | ADL | NDFD | Relative Forage Quality (RFQ) | Milk lbs/Ton | Milk lbs./Acre |
|---|---|---|---|---|---|---|---|---|---|
| CW 95026 | 6.00 | 21.93 | 28.55 | 35.07 | 5.75 | 48.21 | 201 | 3,042 | 18,259 |
| 54V54 | 5.63 | 22.22 | 28.08 | 34.39 | 5.54 | 47.84 | 205 | 3,048 | 17,173 |
| Ameristand 403T | 5.47 | 23.23 | 27.60 | 33.19 | 5.40 | 48.57 | 215 | 3,119 | 17,067 |
| Magnum V | 5.77 | 22.44 | 28.84 | 34.85 | 5.76 | 48.17 | 202 | 3,049 | 17,580 |
| Vernal | 4.71 | 21.67 | 28.47 | 34.66 | 5.51 | 48.69 | 206 | 3,085 | 14,534 |
| WinterGold | 5.50 | 23.21 | 25.78 | 31.47 | 4.99 | 48.81 | 230 | 3,200 | 17,590 |
| WL 325HQ | 5.51 | 23.04 | 27.62 | 33.46 | 5.38 | 47.90 | 211 | 3,075 | 16,929 |
| Trial Mean | 5.63 | 22.79 | 27.46 | 33.32 | 5.37 | 48.35 | 215 | 3,105 | 17,467 |
| LSD (0.05) | 0.46 | 0.79 | 1.50 | 1.70 | 0.36 | 0.88 | 11.80 | 75.62 | 1,303.70 |
| C.V. (%) | 5.81 | 2.45 | 3.87 | 3.61 | 4.71 | 1.29 | 3.88 | 1.72 | 5.28 |
| R2 | 0.77 | 0.61 | 0.51 | 0.55 | 0.56 | 0.51 | 0.64 | 0.53 | 0.77 |

TABLE 22b

Forage Quality of 'CW 95026'. E01WIWS - Spring Forage Yield Trial at West Salem, WI.

| Entry | Total Yield DM tons/acre | CP | ADF | NDF | ADL | NDFD | Relative Forage Quality (RFQ) | Milk lbs/Ton | Milk lbs./Acre |
|---|---|---|---|---|---|---|---|---|---|
| CW 95026 | 6.61 | 20.28 | 35.10 | 42.84 | 7.50 | 44.60 | 144.87 | 2,649.81 | 17,514.41 |
| Europe | 6.29 | 19.28 | 36.10 | 43.81 | 7.67 | 43.45 | 138.00 | 2,600.16 | 16,362.71 |
| Vernal | 5.57 | 19.02 | 36.90 | 44.49 | 7.72 | 44.55 | 137.97 | 2,604.67 | 14,496.89 |
| WinterGold | 6.59 | 20.04 | 34.74 | 42.23 | 7.39 | 44.81 | 148.92 | 2,706.82 | 17,852.38 |
| WL 325HQ | 6.47 | 20.49 | 34.72 | 42.09 | 7.21 | 44.49 | 148.51 | 2,679.75 | 17,333.97 |
| Trial Mean | 6.51 | 19.58 | 35.89 | 43.51 | 7.58 | 44.26 | 141.74 | 2,631.92 | 17,134.80 |
| LSD (0.05) | 0.25 | 1.08 | 1.99 | 2.43 | 0.51 | 0.65 | 11.90 | 97.93 | 928.95 |
| C.V. (%) | 2.76 | 3.90 | 3.92 | 3.95 | 4.74 | 1.03 | 5.93 | 2.63 | 3.83 |
| R2 | 0.90 | 0.54 | 0.37 | 0.33 | 0.31 | 0.62 | 0.33 | 0.35 | 0.84 |

TABLE 23a

Disease Resistance of 'CW 95026'.

| Disease | Level of Resistance |
|---|---|
| Anthracnose | HR |
| *Aphanomyces* Root Rot | HR |
| Bacterial Wilt | HR |
| *Fusarium* Wilt | HR |
| *Phytophthora* Root Rot | HR |
| *Verticillium* Wilt | R |

TABLE 23b

Insect Resistance of 'CW 95026'.

| Insect | Level of Resistance |
|---|---|
| Pea Aphid | HR |
| Spotted Alfalfa Aphid | HR |

TABLE 23c

Nematode Resistance of 'CW 95026'.

| Nematode | Level of Resistance |
|---|---|
| Stem | HR |
| Northern Root Knot | LR |

Example 4

Breeding Methods

The skilled artisan will recognize that the invention of the instant disclosure is not limited to the specific plants and varieties taught herein, but also comprises the use of these plants in methods of breeding alfalfa.

1. Open-Pollinated Populations

The improvement of open-pollinated populations of alfalfa depends essentially upon changing gene-frequencies towards fixation of favorable alleles while maintaining a high (but far from maximal) degree of heterozygosity.

Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, Principles of Plant Breeding, John Wiley & Sons, Inc. (1960); Simmonds, Principles of Crop Improvement, Longman Group Limited (1979); Hallauer and Miranda, Quantitative Genetics in Maize Breeding, Iowa State University Press (1981); and, Jensen, Plant Breeding Methodology, John Wiley & Sons, Inc. (1988). Detailed breeding methodologies specifically applicable to alfalfa are provided in Alfalfa and Alfalfa Improvement, supra.

2. Mass Selection

In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Example 5

Synthetic Alfalfa Varieties

A synthetic variety is produced by crossing a number of selected genotypes, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enter a synthetic vary widely. In practice, numbers of parental lines range from 10 to several hundred, with 100-300 being the average. Broad based synthetics formed from 100 or more clones would be expected to be more stable during seed multiplication than narrow based synthetics.

Synthetics in alfalfa are used in advanced generations as commercial cultivars. The parents are always selected for some particular trait or traits but seldom for combining ability per se. Synthetic cultivars permit the expression of heterosis to a degree, usually less than hybrids, while providing a practical method for seed multiplication.

Parents for synthetic cultivars in alfalfa are selected by many different methods. In an open breeding system the parents can be selected from such diverse sources as ecotypes, cultivars, and experimental strains. Although production of a synthetic cultivar is relatively simple, a wise choice of parents for the Syn 0 generation is crucial, for this will determine the performance of the synthetic. Decisions as to which and how many parents to include, fix the minimum degree of inbreeding that the eventual cultivar will sustain in subsequent generations.

Example 6

Transgenic Alfalfa

One of skill in the art would recognize that the alfalfa plants of the instant invention need not be produced solely by using classical plant breeding methodology. Recombinant DNA techniques allow plant researchers to circumvent the limitations of conventional plant breeding by enabling plant geneticists to identify and clone specific genes for desirable traits. Once the foreign genes have been introduced into a plant, that plant can than be used in conventional plant breeding schemes (e.g., pedigree breeding, single-seed-descent breeding schemes, reciprocal recurrent selection, mass selection, progeny test selection, clonal breeding) to produce progeny which also contain the gene of interest.

Standard techniques well known to those skilled in the art can be used to identify, locate and isolate the genes associated with the improved standability and faster recovery after spring green-up or after harvest obtained in the present invention. Furthermore, the promoters and modifying sequences associated with such genes can also be identified, located and isolated using the same techniques. The isolated nucleic acids can be used to produce transgenic cells, tissues and whole organisms, especially transgenic plant cells, plant tissues and whole plants.

Genes can be introduced in a site directed fashion using homologous recombination. Homologous recombination permits site-specific modifications in endogenous genes and thus inherited or acquired mutations may be corrected, and/or novel alterations may be engineered into the genome.

Homologous recombination and site-directed integration in plants are discussed in U.S. Pat. Nos. 5,451,513, 5,501,967 and 5,527,695.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and *Agrobacterium*-mediated transformation (see, e.g., U.S. Pat. Nos. 5,405,765, 5,472,869, 5,538,877, 5,538,880, 5,550,318, 5,641,664, 5,736,369 and 5,736,369; Watson et al., *Recombinant DNA*, Scientific American Books (1992); Hinchee et al., *Bio/Tech.* 6:915-922 (1988); McCabe et al., *Bio/Tech.* 6:923-926 (1988); Toriyama et al., *Bio/Tech.* 6:1072-1074 (1988); Fromm et al., *Bio/Tech.* 8:833-839 (1990); Mullins et al., *Bio/Tech.* 8:833-839 (1990); and, Raineri et al., *Bio/Tech.* 8:33-38 (1990)).

Transgenic alfalfa plants have been produced by many of these methods including, but not limited to, *agrobacterium*-mediated transformation (Wang et al., *Australian Journal of Plant Physiology* 23(3):265-270 (1996); Hoffman et al., *Molecular Plant-Microbe Interactions* 10(3):307-315 (1997); Trieu et al., *Plant Cell Reports* 16:6-11 (1996)) and particle acceleration (U.S. Pat. No. 5,324,646).

Conner et al. (U.S. Pat. Nos. 6,057,496 and 6,476,291) teach methods for biasing a crop plant which is heterozygous for a transgene towards the production of seeds which carry the transgene, wherein such methods are particularly useful for maintaining a transgene in an alfalfa synthetic variety.

Example 7

Cell and Tissue Culture of Alfalfa

Further reproduction of the alfalfa varieties of the present invention can occur by cell and tissue culture and regeneration. Thus, another aspect of this invention is to provide cells which upon growth and differentiation produce alfalfa plants which have on average about 8% or greater faster recovery after harvest and/or have on average about 15% or greater more erect stems at late bloom when compared to an adapted commercial alfalfa variety grown under the same field growing conditions in North America. Yet another embodiment is a tissue culture of regenerable cells, where the cells include genetic material that convey on average about 8% or greater faster recovery after harvest and/or on average about 15% or greater more erect stems at late bloom when compared to an adapted commercial alfalfa variety grown under the same field growing conditions in North America. Some embodiments include such a tissue culture that includes cultured cells derived, in whole or in part, from a plant part selected from the group consisting of leaves, roots, root tips, root hairs, anthers, pistils, stamens, pollen, ovules, flowers, seeds, embryos, stems, buds, cotyledons, hypocotyls, cells and protoplasts.

In one embodiment, this invention provides cells which upon growth and differentiation produce alfalfa plants having all or substantially all of the physiological and morphological characteristics of alfalfa varieties 'CW 75046'; 'CW 83201'; 'CW 85029'; and 'CW 95026'.

Methods of producing alfalfa plants from tissue culture are well known by the ordinary artisan. See, for example, Daniel C. W. Brown, HortScience 23(3):526-531 (1988); Bingham, E. T., Crop Science 15:719-721 (1975); Fuentes et al., Plant Cell, Tissue and Organ Culture 34:299-302(1993); Hanson et al., Crop Science 27:1084 (1987); Ray et al., Crop Science 29:1545-1548 (1989); Seitz et al., In Vitro Cellular & Developmental Biology 24:1047-1052 (1988); Bingham et al., Alfalfa Tissue Culture, pages 903-929, In *Alfalfa and Alfalfa Improvement*, Hanson et al. (ed.), American Society of Agronomy, Monograph No. 29 (1988); and U.S. Pat. Nos. 5,324,646; 5,731,202; 5,908,974; 5,994,626; 6,127,599; 6,143,951; 6,359,195; 6,563,019 and 6,566,137, each of which is incorporated herein in their entirety.

Initiation of callus from immature anthers, immature ovaries, cotyledons, internode sections, and seedling hypocotyls of 'CW 75046', 'CW 83201', 'CW 85029' and/or 'CW 95026' can be achieved on Blaydes medium supplemented with various combinations and concentrations of kinetin (K), ∀-naphthalene acetic acid (NAA), and 2,4-dichlorophenoxyacetic acid (2,4-D). See, for example, Saunders, J. W. and E. T. Bingham, Crop Science 12(6): 804-808 (1972). Whole alfalfa plants can be produced from the callus tissue, wherein the alfalfa plants have the same or substantially the same morphological and physiological characteristics as the plant from which the calli were derived.

The foregoing detailed description has been given for clearness of understanding only and no unnecessary limitations should be understood therefrom as modifications will be obvious to those skilled in the art.

Ratings are based on the average performance of a variety grown over a wide range of climate and soil types within its adapted maturity under normal growing conditions. Extreme conditions may adversely affect performance.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. An alfalfa variety designated 'CW 75046', representative seed of which has been deposited as ATCC Accession No. PTA-5346, wherein said alfalfa variety has about 15% or greater more erect stems at late bloom compared to an adapted commercial variety grown under the same field growing conditions in North America, wherein the adapted commercial variety is selected from the group consisting of 'WinterGold', 'WL325HQ', 'WL319HQ' and 'Hybri-Force 400'.

2. An alfalfa variety designated 'CW 95026', representative seed of which has been deposited as ATCC Accession No. PTA-5349, wherein said alfalfa variety has about 15% or greater more erect stems at late bloom compared to an adapted commercial variety grown under the same field growing conditions in North America, wherein the adapted commercial variety is selected from the group consisting of 'WinterGold', 'WL325HQ', 'WL319HQ' and 'Hybri-Force 400'.

3. A tissue culture of regenerable cells of alfalfa variety designated 'CW 75046', representative seed of which has been deposited as ATCC Accession No. PTA-5346, wherein the cells regenerate plants having about 15% or greater more erect stems at late bloom compared to at least one adapted commercial variety grown under the same field growing conditions in North America, wherein the adapted commercial variety is selected from the group consisting of 'WinterGold', 'WL325HQ', 'WL319HO' and 'Hybri-Force 400'.

4. A tissue culture of regenerable cells of alfalfa variety designated 'CW 95026', representative seed of which has been deposited as ATCC Accession No. PTA-5349, wherein the cells regenerate plants having about 15% or greater more erect stems at late bloom compared to at least one adapted commercial variety grown under the same field growing conditions in North America, wherein the adapted commercial variety is selected from the group consisting of 'WinterGold', 'WL325HQ', 'WL319HO' and 'Hybri-Force 400'.

* * * * *